(12) United States Patent
Müller et al.

(10) Patent No.: US 8,309,742 B2
(45) Date of Patent: Nov. 13, 2012

(54) USE OF THE PIGD PROTEIN FOR CATALYZING 1,4-ADDITIONS OF 2-OXOALKANOATES TO α, β-UNSATURATED KETONES

(75) Inventors: Michael Müller, Gundelfingen (DE); Carola Dresen, Freiburg (DE); Michael Richter, Freiburg (DE)

(73) Assignee: Albert-Ludwigs-Universitat Freiburg, Freiburg (DE)

( * ) Notice: Subject to any disclaimer, the term of this patent is extended or adjusted under 35 U.S.C. 154(b) by 316 days.

(21) Appl. No.: 12/599,373

(22) PCT Filed: Apr. 18, 2008

(86) PCT No.: PCT/EP2008/003152
§ 371 (c)(1),
(2), (4) Date: Feb. 25, 2010

(87) PCT Pub. No.: WO2008/138450
PCT Pub. Date: Nov. 20, 2008

(65) Prior Publication Data
US 2010/0305337 A1 Dec. 2, 2010

(30) Foreign Application Priority Data

May 9, 2007 (DE) .......................... 10 2007 021 698

(51) Int. Cl.
*C07D 333/22* (2006.01)
(52) U.S. Cl. ........................................................ 549/78
(58) Field of Classification Search .................. 549/502, 549/78
See application file for complete search history.

(56) References Cited

OTHER PUBLICATIONS

Williamson, et al. "Biosynthesis of the Red Antibiotic, Prodigiosin, in Serratia: Identification of a Novel 2-methyl-3-n-amyl-pyrole (MAP) Assembly Pathway, Definition of the Terminal Condensing Enzyme, and Implications for Undecylprodigiosin Biosynthesis in Streptomyces", Molecular Microbiology, vol. 56 (4), pp. 971-989 (May 2005).
Harris, et al. "Putative Uncharacterized Protein PigD", Database EMBL, Accession No. Q5W251 (Dec. 2004).

*Primary Examiner* — Taofiq A Solola
(74) *Attorney, Agent, or Firm* — Chalin A. Smith; Smith Patent Consulting

(57) ABSTRACT

The present invention relates to the preparation of compounds of the general formula II

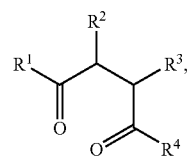

which can be obtained by 1,4 addition of 2-oxoalkanoates or 2-oxocarboxylic acids onto the appropriate ketones. The present invention also relates to the use of the PigD protein for catalysis of 1,4 additions of 2-oxoalkanoates/-carboxylic acids, for example pyruvate/pyruvic acid or 2-oxobutyrate/2-oxobutyric acid, onto aliphatic, aromatic and heterocyclic α,β-unsaturated ketones. The 1,4 additions are effected here with $CO_2$ elimination. The use of the PigD protein as a catalyst in the aforementioned 1,4 additions enables the synthesis of addition products with stereoactive centers these addition products being preparable with an enantiomeric excess of more than 80% ee. The aliphatic, aromatic and heterocyclic α,β-unsaturated ketones which are suitable for the process are represented by the general formula I:

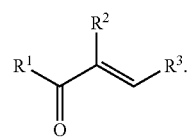

7 Claims, 14 Drawing Sheets

(E)-4-(4-chlorophenyl)-
but-3-en-2-one 2-oxobutanoate 4-(4-chlorophenyl)heptane-2,5-dione (E)-non-3-en-2-one
140 g/mol pyruvate 3-pentylhexane-2,5-dione
184 g/mol (E)-dec-3-en-2-one
154 g/mol pyruvate 3-hexylhexane-2,5-dione
198 g/mol

SEQUENCE LISTING

<160> NUMBER OF SEQ ID NOS: 2

<210> SEQ ID NO 1
<211> LENGTH: 903
<212> TYPE: PRT
<213> ORGANISM: Serratia marcescens

<400> SEQUENCE: 1

```
Met Arg Ala Ala Thr Ala Ala Cys Arg Asp Arg Arg Gly Leu Cys Arg
1               5                   10                  15

Ala Glu Phe Ala Arg Leu Ala Glu Ala Val Thr Pro Phe Trp Leu His
            20                  25                  30

Lys Glu Leu Ile Met Thr Thr Leu Thr Gly Gln Ala Arg Leu Thr Asn
        35                  40                  45

Ser Ala Ala Tyr Glu Gln Val Trp Gln Ala Glu Arg Gln Ala Cys Arg
    50                  55                  60

Thr Asp Ala Asp Pro Asp Thr Leu Thr Val Gly Val Val Val Val Thr
65                  70                  75                  80
```

```
Arg Asn Pro Ala Phe Phe Gln Thr Gly Leu Ser Val Leu Asn Asp Ile
                85                  90                  95
Arg Asp Tyr Val Phe Asn Arg Val His Ile Gln Ser Glu Met Pro Leu
            100                 105                 110
Lys Leu Leu Asp Leu Ala Ala Asp Ser Leu Tyr Leu Ala Ala Arg Glu
        115                 120                 125
Lys Ala Leu His Phe Leu Lys Gly Gln Asn Lys Ala Ile Asn Val Arg
    130                 135                 140
Ile Ile Gln Cys Ala Ser Leu Ala Glu Ala Thr Gly Lys Ile Ile Tyr
145                 150                 155                 160
Thr His Ala Leu Glu Gln Arg Pro Glu Phe His Leu Gly Met Leu Phe
                165                 170                 175
Tyr Asp Gln Thr Thr Pro Ala Gly Val Asp Asp Ser Ile Glu Gln Ile
            180                 185                 190
Asp Arg Asp Leu Asp Ala Phe Tyr Ser Ala Leu Gln Arg Ser Gly Ile
        195                 200                 205
Pro Ala Phe Tyr Thr Thr Phe Ser Thr Val Ala Phe Ile Arg Gln Leu
    210                 215                 220
Arg Ser Pro Phe Arg Tyr Leu Pro Gln Gln Tyr Arg Glu Ile Val Arg
225                 230                 235                 240
Ser Glu Asp Pro Ala Ile Phe Gln Thr Glu Leu Leu Cys Leu Trp Met
                245                 250                 255
Asp Phe Phe Glu Met Asn Tyr Thr Asn Arg Arg Val Lys Pro Ile Gly
            260                 265                 270
Ala Leu Ala Leu His Asn Thr Leu Gly Glu Gln Leu Ile Gln Phe Phe
        275                 280                 285
Glu Arg Thr Ala Ala Glu Arg Trp Leu Val Ser Tyr Tyr Thr Gly Ser
    290                 295                 300
Ile Ile Ser Asn Leu Ile Gly Tyr Leu Asp Arg His Ala Glu Ala Arg
305                 310                 315                 320
Gly Ala Leu Ile Leu Arg Gly Pro Asn Glu His Ala Ile Ala Cys Gly
                325                 330                 335
Ala Met Ala Asn Trp Gln Leu Tyr Arg Met Pro Phe Leu Gly Val Val
            340                 345                 350
Thr Ser Gly Met Met Asp Glu Phe Lys Gly Thr Leu Ala Asn Leu Lys
        355                 360                 365
Glu Thr Ala Ala Gln Gly Ile Ile Val Ala Ala Glu Asn Arg Gly Asn
    370                 375                 380
Gln Trp Tyr Ser Phe Gln Gly Thr Leu Thr Pro Thr Glu Asp Met Arg
385                 390                 395                 400
Glu Val Leu Ile Ala Arg Arg Ile Pro Phe Val Tyr Ile Asp Asp Val
                405                 410                 415
Glu Met Ile Gly Ala Gly Leu Thr Glu Ala Phe Arg Leu Tyr His Gln
            420                 425                 430
Gly Gln Gly Pro Val Val Ile Leu Ala Thr Gln Asn Val Leu Glu Ser
        435                 440                 445
Thr Leu Ser Leu Glu Gly Ala Val Cys Asp Pro Ser Pro Ile Pro Val
    450                 455                 460
Leu Ser Ala Asp Asp Pro Leu Pro Met Ser Glu Ser Leu Ala Gln Ala
465                 470                 475                 480
Ile Ala Leu Ile Asn Arg Gly Pro Glu Arg Leu Val Trp Gln Leu Gly
                485                 490                 495
Pro Val Ser Asp Asp Glu Tyr Ala Leu Ile His Asp Ile Ala Asp Ala
            500                 505                 510
```

Ala Gly Ile Ala Leu Val Asp Ser Leu Ala His Pro Gly Ser Ala Pro
        515                 520                 525

Lys Tyr Tyr Gln Gly Arg Arg Asn Pro His Tyr Leu Gly Thr Leu Ala
    530                 535                 540

Ile Tyr Gly Tyr Ser Pro Arg Val Tyr Asn Phe Leu His Thr Asn Asp
545                 550                 555                 560

Lys Leu Asn Ala Met Ser Glu Gln Ser Leu Phe Met Ile Lys Ser Arg
                565                 570                 575

Val Ala Gln Ile Thr Thr Pro Phe Ser Asp Gly Arg Leu Glu Arg Lys
            580                 585                 590

Val His Leu Val Gln Leu Thr His Asp Asp Arg His Leu Ser Pro Tyr
        595                 600                 605

Ala Asp Leu His Leu His Met Asn Cys Leu Ala Phe Leu Arg Thr Val
    610                 615                 620

Lys Ala His Leu Asp Val Asp Pro Ala Leu Arg Glu Arg Arg Arg Ala
625                 630                 635                 640

Leu Ile Ala Ala Tyr Leu Asp Ser Pro Ser Asp Val Val Ser Gln Leu
                645                 650                 655

Pro Ser Leu Pro Met Ser Ala Asn Tyr Phe Phe Cys Gln Leu Asn Arg
            660                 665                 670

Val Ile Glu Glu Leu Ile Glu Thr Glu Gly Phe Asp Phe Thr Gly Val
        675                 680                 685

Tyr Asp Val Gly Arg Cys Gly Ile Ser Ala Ala Arg Asn Val Ala Lys
    690                 695                 700

Thr Arg Arg Gly Phe Ser Gly Trp Tyr Gly Arg Ala Leu Met Gly Asp
705                 710                 715                 720

Ala Leu Leu Ala Thr Gly Tyr Leu Ala Tyr Thr Ser Pro Ser His Val
                725                 730                 735

Met Ala Phe Ile Gly Asp Gly Ala Lys Gly Ile Val Pro Asp Ile Leu
            740                 745                 750

Pro Ala Phe Ile Asp Asn Ile Leu Thr His Pro Gln Leu Leu Asn Lys
        755                 760                 765

Ser Ile Thr Val Phe Tyr Leu Cys Asn Gly Gly Leu Ser Val Ile Asn
    770                 775                 780

Thr Tyr Gln Glu Arg Ile Leu Phe Asn Arg Thr Ser Arg Gln Met Arg
785                 790                 795                 800

Leu Val Asn Val Glu Gln Pro Asp Val Glu Gln Thr Val Asn Asn Phe
                805                 810                 815

His Ile Gln Ser Lys Thr Leu Thr His Phe Asp Glu Asp Val Ile Arg
            820                 825                 830

Gln Ala Leu Thr Thr Pro His Arg Leu Asn Leu Phe Ser Val Val Leu
        835                 840                 845

Gly His Asn Asn Glu Gly Asp Gly Ile Ser Leu Ala Thr Ala Lys Gly
    850                 855                 860

Trp Gln Arg Asp Pro Ser Asp His Asp Ala Leu Gln Glu Arg Lys Ala
865                 870                 875                 880

Trp Ala Ala Gln Gln Pro Glu Ser Thr Ser Thr Ala Phe Asp Gln Asp
                885                 890                 895

Pro Thr Gln Glu Ala Thr Ser
            900

<210> SEQ ID NO 2
<211> LENGTH: 904
<212> TYPE: PRT

<213> ORGANISM: Serratia marcescens

<400> SEQUENCE: 2

```
Met Arg Ala Ala Thr Ala Ala Cys Arg Asp Arg Arg Gly Leu Cys Arg
1               5                   10                  15

Ala Glu Phe Ala Arg Leu Ala Glu Ala Val Thr Pro Phe Trp Leu His
            20                  25                  30

Lys Glu Leu Ile Met Thr Thr Leu Thr Gly Gln Ala Arg Leu Thr Asn
        35                  40                  45

Ser Ala Ala Tyr Glu Gln Val Trp Gln Ala Glu Arg Gln Ala Cys Arg
    50                  55                  60

Thr Asp Ala Asp Pro Asp Thr Leu Thr Val Gly Val Val Val Val Thr
65                  70                  75                  80

Arg Asn Pro Ala Phe Phe Gln Thr Gly Leu Ser Val Leu Asn Asp Ile
                85                  90                  95

Arg Asp Tyr Val Phe Asn Arg Val His Ile Gln Ser Glu Met Pro Leu
            100                 105                 110

Lys Leu Leu Asp Leu Ala Ala Asp Ser Leu Tyr Leu Ala Ala Arg Glu
        115                 120                 125

Lys Ala Leu His Phe Leu Lys Gly Gln Asn Lys Ala Ile Asn Val Arg
    130                 135                 140

Ile Ile Gln Cys Ala Ser Leu Ala Glu Ala Thr Gly Lys Ile Ile Tyr
145                 150                 155                 160

Thr His Ala Leu Glu Gln Arg Pro Glu Phe His Leu Gly Met Leu Phe
                165                 170                 175

Tyr Asp Gln Thr Thr Pro Ala Gly Val Asp Asp Ser Ile Glu Gln Ile
            180                 185                 190

Asp Arg Asp Leu Asp Ala Phe Tyr Ser Ala Leu Gln Arg Ser Gly Ile
        195                 200                 205

Pro Ala Phe Tyr Thr Thr Phe Ser Thr Val Ala Phe Ile Arg Gln Leu
    210                 215                 220

Arg Ser Pro Phe Arg Tyr Leu Pro Gln Gln Tyr Arg Glu Ile Val Arg
225                 230                 235                 240

Ser Glu Asp Pro Ala Ile Phe Gln Thr Glu Leu Leu Cys Leu Trp Met
                245                 250                 255

Asp Phe Phe Glu Met Asn Tyr Thr Asn Arg Arg Val Lys Pro Ile Gly
            260                 265                 270

Ala Leu Ala Leu His Asn Thr Leu Gly Glu Gln Leu Ile Gln Phe Phe
        275                 280                 285

Glu Arg Thr Ala Ala Glu Arg Trp Leu Val Ser Tyr Tyr Thr Gly Ser
    290                 295                 300

Ile Ile Ser Asn Leu Ile Gly Tyr Leu Asp Arg His Ala Glu Ala Arg
305                 310                 315                 320

Gly Ala Leu Ile Leu Arg Gly Pro Asn Glu His Ala Ile Ala Cys Gly
                325                 330                 335

Ala Met Ala Asn Trp Gln Leu Tyr Arg Met Pro Phe Leu Gly Val Val
            340                 345                 350

Thr Ser Gly Met Met Asp Glu Phe Lys Gly Thr Leu Ala Asn Leu Lys
        355                 360                 365

Glu Thr Ala Ala Gln Gly Ile Ile Val Ala Ala Glu Asn Arg Gly Asn
    370                 375                 380

Gln Trp Tyr Ser Phe Gln Gly Thr Leu Thr Pro Thr Glu Asp Met Arg
385                 390                 395                 400

Glu Val Leu Ile Ala Arg Arg Ile Pro Phe Val Tyr Ile Asp Asp Val
```

-continued

```
            405                 410                 415
Glu Met Ile Gly Ala Gly Leu Thr Glu Ala Phe Arg Leu Tyr His Gln
                420                 425                 430
Gly Gln Gly Pro Val Val Ile Leu Ala Thr Gln Asn Val Leu Glu Ser
            435                 440                 445
Thr Leu Ser Leu Glu Gly Ala Val Cys Asp Pro Ser Pro Ile Pro Val
450                 455                 460
Leu Ser Ala Asp Asp Pro Leu Pro Met Ser Glu Ser Leu Ala Gln Ala
465                 470                 475                 480
Ile Ala Leu Ile Asn Arg Gly Pro Glu Arg Leu Val Trp Gln Leu Gly
                485                 490                 495
Pro Val Ser Asp Asp Glu Tyr Ala Leu Ile His Asp Ile Ala Asp Ala
                500                 505                 510
Ala Gly Ile Ala Leu Val Asp Ser Leu Ala His Pro Gly Ser Ala Pro
                515                 520                 525
Lys Tyr Tyr Gln Gly Arg Arg Asn Pro His Tyr Leu Gly Thr Leu Ala
            530                 535                 540
Ile Tyr Gly Tyr Ser Pro Arg Val Tyr Asn Phe Leu His Thr Asn Asp
545                 550                 555                 560
Lys Leu Asn Ala Met Ser Glu Gln Ser Leu Phe Met Ile Lys Ser Arg
                565                 570                 575
Val Ala Gln Ile Thr Thr Pro Phe Ser Asp Gly Arg Leu Glu Arg Lys
                580                 585                 590
Val His Leu Val Gln Leu Thr His Asp Asp Arg His Leu Ser Ala Tyr
            595                 600                 605
Ala Asp Leu His Leu His Met Asn Cys Leu Ala Phe Leu Arg Thr Val
            610                 615                 620
Lys Ala His Leu Asp Val Asp Pro Ala Leu Arg Glu Arg Arg Arg Ala
625                 630                 635                 640
Leu Ile Ala Ala Tyr Leu Asp Ser Pro Ser Asp Val Val Ser Gln Leu
                645                 650                 655
Pro Ser Leu Pro Met Ser Ala Asn Tyr Phe Phe Cys Gln Leu Asn Arg
            660                 665                 670
Val Ile Glu Glu Leu Ile Glu Thr Glu Gly Phe Asp Phe Thr Gly Val
            675                 680                 685
Tyr Asp Val Gly Arg Cys Gly Ile Ser Ala Ala Arg Asn Val Ala Lys
            690                 695                 700
Thr Arg Arg Gly Phe Ser Gly Trp Tyr Gly Arg Ala Leu Met Gly Asp
705                 710                 715                 720
Ala Leu Leu Ala Thr Gly Tyr Leu Ala Tyr Thr Ser Pro Ser His Val
                725                 730                 735
Met Ala Phe Ile Gly Asp Gly Ala Lys Gly Ile Val Pro Asp Ile Leu
                740                 745                 750
Pro Ala Phe Ile Asp Asn Ile Leu Thr His Pro Gln Leu Leu Asn Lys
            755                 760                 765
Ser Ile Thr Val Phe Tyr Leu Cys Asn Gly Gly Leu Ser Val Ile Asn
            770                 775                 780
Thr Tyr Gln Glu Arg Ile Leu Phe Asn Arg Thr Ser Arg Gln Met Arg
785                 790                 795                 800
Leu Val Asn Val Glu Gln Pro Asp Val Glu Gln Thr Val Asn Asn Phe
                805                 810                 815
His Ile Gln Ser Lys Thr Leu His Phe Asp Glu Asp Val Ile Arg
                820                 825                 830
```

| | | | | | | | | | | | | | |
|---|---|---|---|---|---|---|---|---|---|---|---|---|---|
| Gln | Ala | Leu | Thr | Thr | Ser | His | Arg | Leu | Asn | Leu | Phe | Ser | Val Val Leu |
| | | 835 | | | | | 840 | | | | | 845 | |
| Gly | His | Asn | Asn | Glu | Gly | Asp | Gly | Ile | Ser | Pro | Gly | His | Arg Gln Arg |
| 850 | | | | | | 855 | | | | | | 860 | |
| Leu | Ala | Ala | Leu | Ile | Arg | Ala | Asp | His | Asp | Ala | Leu | Gln | Glu Arg Lys |
| 865 | | | | | 870 | | | | | 875 | | | 880 |
| Ala | Trp | Ala | Ala | Gln | Gln | Pro | Glu | Ser | Thr | Ser | Thr | Ala | Phe Asp Gln |
| | | | | 885 | | | | | 890 | | | | 895 |
| Asp | Pro | Thr | Gln | Glu | Ala | Thr | Ser | | | | | | |
| | | | 900 | | | | | | | | | | |

USE OF THE PIGD PROTEIN FOR CATALYZING 1,4-ADDITIONS OF 2-OXOALKANOATES TO α, β-UNSATURATED KETONES

This application corresponds to the national phase of International Application No. PCT/EP2008/003152 filed Apr. 18, 2008, which, in turn, claims priority to German Patent Application No. 10 2007 021 698.1 filed May 9, 2007, the contents of which are incorporated by reference herein in their entirety.

The present invention relates to the preparation of compounds of the formula II (see below), which can be obtained by the 1,4 addition of 2-oxoalkanoates onto the appropriate ketones. The present invention also relates to the use of the PigD protein for catalysis of 1,4 additions of 2-oxoalkanoates and 2-oxocarboxylic acids, for example, pyruvate/pyruvic acid or 2-oxobutyrate/-butyric acid, onto aliphatic, aromatic and heterocyclic, α,β-unsaturated ketones. The 1,4 additions are effected here with elimination of $CO_2$. The use of the PigD protein as a catalyst in the aforementioned 1,4 additions enables the synthesis of addition products with stereoactive or chiral centers, the addition products being preparable with an enantiomeric excess of more than 90% ee. The aliphatic, aromatic and heterocyclic α,β-unsaturated ketones which are suitable for the process are represented by formula I (see below).

The Stetter reaction is the 1,4 addition of aldehydes onto α,β-unsaturated carbonyl compounds (Stetter, Angewandte Chemie-International Edition 1976, 15, 639; Stetter et al., Organic Reactions, 1991, 40, 407). With the aim of performing the Stetter reaction asymmetrically, various chiral catalysts have been developed in the past decades (Christmann, Angewandte-Chemie-International Edition 2005, 44, 2632). The intramolecular, but in particular the intermolecular, asymmetric Stetter reaction constitutes a great challenge. To date, it is possible with organic catalysts to perform the intermolecular 1,4 addition with a maximum 4% yield and an enantiomeric excess of only 39%, with the catalyst concentration significantly above the catalytic range. Catalyst and substrate form stable addition products here, a conceivable explanation why the activity always remains low according to Enders et al. (Enders et al., Accounts of Chemical Research 2004, 37, 534).

One alternative to the known processes for performing the Stetter reaction might be the use of enzymes as catalysts. It has been postulated, for example, that the reaction of 2-octenal with pyruvate to give 3-acetyloctanal in one stage of the biosynthesis of the secondary metabolite prodigiosin in the white phenotype of Serratia marcescens is catalyzed by the PigD protein (Salmond et al., Molecular Microbiology 2005, 56, 971):

As is evident from the publication cited above, the PigD protein probably catalyzes the elimination of $CO_2$ from pyruvate and the addition thereof onto 2-octenal in the 1,4 position (see FIG. 1).

Nothing is known to date about the stereoselectivity of this reaction. If this 1,4 activity of the PigD protein were to be present with respect to α,β-unsaturated carbonyl compounds, an intermolecular Stetter reaction could be performed using the PigD protein as a catalyst.

In the context of the present invention, it has, however, been found, surprisingly, that the reaction of 2-octenal in the E configuration with pyruvate under PigD protein catalysis does not lead, as described by Salmond et al. to a 1,4 addition product, but to a 1,2 addition product. FIG. 2 shows the PigD catalyzed reaction of 2-octenal and 2-hexenal with pyruvate. This states the amount of product determined by means of NMR (nuclear magnetic resonance) and the enantiomeric excess (determined by means of chiral HPLC—high performance liquid chromatography) in percent. The experimental data therefore show that the PigD protein has a 1,2 activity. The biosynthesis of the secondary metabolite prodigiosin must consequently proceed by another reaction route.

It is known that pyruvate decarboxylases from Saccharomyces cerevisiae, Acetobacter pasteurianus and Zymomonas mobilis catalyze C—C bond formation of aromatic and aliphatic aldehydes in the 1,2 position (Bornemann et al., Journal of the Chemical Society-Perkin Transactions 1 1993, 309; M. Pohl, Adv. Biochem. Eng. Biotechnol. 1997, 58, 15; Iding et al., Biochimica et Biophysica Acta-Protein Structure and Molecular Enzymology 1998, 1385, 307; Siegert et al., Protein Engineering Design & Selection 2005, 18, 345). It was therefore to be expected that they are capable, just like the PigD protein, of catalyzing C—C bond formation in the 1,2 position in α,β-unsaturated aliphatic aldehydes (FIG. 3).

Further reactions regarding the catalysis behavior of the pigD protein in the context of the present invention showed that aromatic aldehydes can also be reacted with pyruvate, for example to give phenylacetylcarbinols. Such a reaction is also known for the pyruvate decarboxylase from Saccharomyces cerevisiae (see FIG. 4) (Iding et al., Biochimica et Biophysica Acta-Protein Structure and Molecular Enzymology 1998, 1385, 307). In FIG. 4, "scPDC" stands for Saccharomyces cerevisiae pyruvate decarboxylase.

In addition, it is known that the pyruvate decarboxylases from Zymomonas mobilis and Acetobacter pasteurianus also catalyze the addition of pyruvate onto benzaldehyde and 2-octenal in the manner of a 1,2 addition.

In addition, the pigD protein catalyzes, in the absence of an electrophile, for example, an aldehyde, the reaction of two pyruvate molecules with one another (see FIG. 5). This reactivity was also found in various pyruvate decarboxylases, for example, decarboxylases from Zymomonas mobilis ((S)-acetoin) or Saccharomyces cerevisiae ((R)-acetoin) (Bornemann et al., Journal of the Chemical Society-Perkin Transactions 1 1993, 309).

According to the sequence analysis, the PigD protein is a thiamine diphosphate-dependent enzyme with homology to an acetolactate synthase (Marchler-Bauer et al., Nucleic Acid Res 2004, 32, 327).

Owing to the aforementioned catalytic properties of the PigD protein and the similarities to the known pyruvate decarboxylases, it is possible to draw the conclusion that the PigD protein is a pyruvate decarboxylase.

The pyruvate decarboxylases are incapable of enabling additions onto α,β-unsaturated ketones. The pyruvate decarboxylases can use only aldehydes as the substrate. The lack of reactivity with respect to ketones can be explained by the fact that they have a greatly reduced carbonyl activity and a greater steric hindrance with respect to the active site of the enzymes compared to aldehydes.

Since the reworking of the reaction of 2-octenal with pyruvate unexpectedly did not provide the 1,4 addition product described by Salmond et al., it was therefore to be expected that the PigD protein, like the other decarboxylases, is suitable only for catalysis of 1,2 additions.

It was additionally to be expected that the PigD protein, like the other pyruvate decarboxylases too, is incapable of catalyzing additions onto α,β-unsaturated ketones.

It is therefore an object of the present invention to enable a 1,4 addition of 2-oxoalkanoates/-carboxylic acids onto α,β-unsaturated ketones with a high enantiomeric excess and a good yield. This affords products with R configuration when $R^3$ is an aromatic ($R^3$ is bonded via an $sp^2$-hybridized carbon).

In the case of an aliphatic ($R^3$ is bonded via an $sp^3$-hybridized carbon), the determination of configuration is formally reversed.

It has now been found that, unexpectedly, the PigD protein, contrary to the expected properties, is capable of catalyzing 1,4 additions of 2-oxoalkanoates/-carboxylic acids onto aliphatic, aromatic and heterocyclic α,β-unsaturated ketones with $CO_2$ elimination. The object of the invention is therefore surprisingly achieved by the use of the PigD protein as a catalyst.

The present invention therefore relates to a process for preparing compounds of the formula II

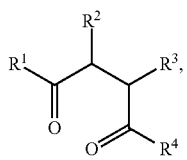

II characterized in that compounds of the formula I

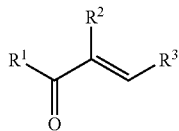

I are reacted with 2-oxoalkanoates/-carboxylic acids of the formula $R^4C(O)COO^-/R^4C(O)COOH$,
in which $R^1$ is a straight-chain or branched, preferably straight-chain, $C_1$-$C_{10}$-alkyl radical or an aromatic, where the aromatic is more preferably a phenyl group,
$R^2$ is a hydrogen, an alkyl radical, preferably a $C_1$-$C_{10}$-alkyl radical, or an aromatic where the aromatic is more preferably a phenyl group,
$R^3$ is a straight-chain or branched $C_1$-$C_{10}$-alkyl radical, a heterocycle or an aromatic, where the $C_1$-$C_{10}$-alkyl radical may in turn have a heterocycle or an aromatic, and where the heterocycle or the aromatic may be substituted by methoxy groups, halogens or hydroxyl groups, where the aromatic is more preferably a phenyl group, and
$R^4$ is an alkyl radical, preferably $C_1$-$C_{10}$-alkyl radical,
and in which, the PigD protein is used as a catalyst. It is additionally more preferred that $R^1$ is a saturated alkyl radical. Even more preferably, the compounds of the formula I are used in the E configuration.

In an even further preferred embodiment of the process, $R^1$ is a methyl group or a phenyl group, $R^2$ is a hydrogen, an alkyl group, preferably a $C_1$-$C_4$-alkyl radical, more preferably a methyl group, or a phenyl group, $R^3$ is a $C_1$-$C_{10}$-alkyl group, a heterocycle or an aromatic, which may be substituted by methoxy groups, halogens or hydroxyl groups, and $R^4$ is a $C_1$-$C_{10}$-hydrocarbon. The aromatic here is more preferably a phenyl group. The $C_1$-$C_{10}$-alkyl group is preferably a saturated alkyl group.

In another preferred embodiment of the process, the 1,4 addition is effected enantioselectively with an enantiomeric excess of more than 80% ee. More preferably, the 1,4 addition is effected enantioselectively with an enantiomeric excess of more than 90% ee and most preferably with an enantiomeric excess of more than 98% see.

In a further preferred embodiment of the process, straight-chain, saturated 2-oxoalkanoates/-carboxylic acids with 1-10 carbon atoms are used as donor substrates.

In another preferred embodiment of the process, pyruvate or pyruvic acid or 2-oxobutanoate or 2-oxybutyric acid is used as the donor substrate, and $R^4$ is methyl or ethyl. More preferably, pyruvate or pyruvic acid is used as the donor substrate.

The present invention also relates to the use of the PigD protein for catalysis of 1,4 additions of 2-oxoalkanoates or 2-oxocarboxylic acids onto α,β-unsaturated ketones of the formula I

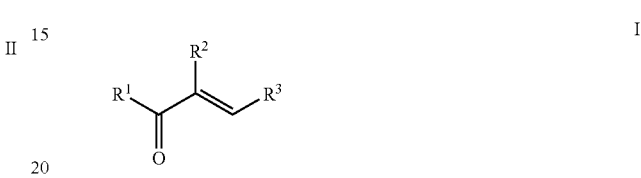

in which $R^1$ is a straight-chain or branched $C_1$-$C_{10}$-alkyl radical or an aromatic,
$R^2$ is a hydrogen or aromatic, where the aromatic is preferably a phenyl group,
$R^3$ is a straight-chain or branched $C_1$-$C_{10}$-alkyl radical, a heterocycle or an aromatic, where the $C_1$-$C_{10}$-alkyl radical may in turn have a heterocycle or an aromatic, and where the heterocycle or the aromatic may be substituted by methoxy groups, halogens or hydroxyl groups, and
wherein the 1,4 additions are effected with $CO_2$ elimination. More preferably the compounds of the formula I are used in the E configuration.

The $R^1$, $R^2$ and $R^3$ radicals may be defined identically in the preparation process according to the present invention and in the process for using the PigD protein.

A preferred embodiment of the use of the PigD protein is characterized in that pyruvate/pyruvic acid or 2-oxobutanoate/-butyric acid is used as the 2-oxoalkanoate.

A further preferred embodiment of the use of the PigD protein is characterized in that the 1,4 additions are effected enantioselectively with an enantiomeric excess of the addition products of more than 80% ee, more preferably of more than 90% ee and most preferably with an enantiomeric excess of the addition products of more than 98% ee.

Another preferred embodiment of the use of the PigD protein is characterized in that aliphatic, aromatic and heterocyclic α,β-unsaturated ketones of the formula I are used, in which $R^1$ is a methyl group or an aromatic, where the aromatic is preferably a phenyl group, $R^2$ is a hydrogen atom, an alkyl group or aromatic, more preferably a hydrogen atom or aromatic, and $R^3$ is a $C_1$-$C_{10}$-alkyl group, a heterocycle or a phenyl group, where the heterocycle and the phenyl group may be substituted by methoxy groups, halogens or hydroxyl groups.

Surprisingly, it is possible by the inventive reaction to perform a 1,4 addition of 2-oxoalkanoates or 2-oxocarboxylic acids onto aliphatic straight-chain or branched α,β-unsaturated ketones (see FIG. 6) with a very high enantiomeric excess (see examples). In addition, the amount of by-products (from the reaction of the 2-oxoalkanoates/-carboxylic acids with one another) in the case of use of the PigD protein remains low.

In addition, it is possible by the inventive reaction to perform a 1,4 addition of 2-oxoalkanoates/-carboxylic acids onto aromatic α,β-unsaturated ketones (see FIG. 7) with a high enantiomeric excess.

It is likewise possible in an advantageous manner, proceeding from α,β-unsaturated heterocyclic ketones, using the PigD protein, to prepare 1,4-diketones (see FIG. 8).

In an advantageous manner, it is additionally also possible to use other 2-oxoalkanoates/-carboxylic acids, for example 2-oxobutanoate/-butyric acid (see FIG. 9).

The PigD protein catalyzes 1,4 additions of 2-oxoalkanoates/-carboxylic acids onto aliphatic, aromatic and heterocyclic α,β-unsaturated ketones with elimination of $CO_2$ (see equation 1; equation 1 shows only the use of 2-oxoalkanoates; 2-oxocarboxylic acids can likewise be used). The $R^4$ radical in the general formula for the 2-oxoalkanoates/-carboxylic acid represents straight-chain or branched, preferably straight-chain, alkyl radicals, preferably straight-chain or branched, preferably straight-chain (e.g. methyl, ethyl, propyl, butyl, pentyl, etc.), $C_1$-$C_{10}$-alkyl radicals.

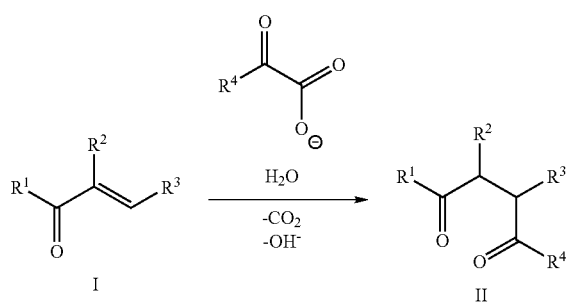

(1)

By the inventive reaction, it is possible to react 2-oxoalkanoates/-carboxylic acids with compounds of the formula I to give compounds of the formula II. The description of the reaction is therefore always based both on the use of the PigD protein for catalysis of the inventive 1,4 additions and on the preparation of compounds of the formula II using the inventive 1,4 additions.

The PigD protein catalyzes the inventive reaction stereoselectively. The newly formed stereoactive or chiral center is preferably formed with an enantiomeric excess of at least 80% ee, more preferably at least 86% ee, more preferably at least 90% ee, more preferably at least 94% ee, more preferably at least 98% ee.

The expression "PigD protein" as used here encompasses proteins which have essentially the amino acid sequences according to SEQ ID NO: 1 (modified PigD protein; see examples) or SEQ ID NO: 2 (known PigD protein, EMBL database number: CAH55649.1) (see sequence listing). The PigD protein more preferably has essentially the amino acid sequence according to SEQ ID NO: 1.

The expression "PigD protein" likewise encompasses protein variants of the sequence according to SEQ ID NO: 1, for example owing to allelic variations. These variants may have mutations from the sequence according to SEQ ID NO: 1, for example substitutions, additions and/or deletions. In this context, it is possible for preferably 1-30, more preferably 1-25, more preferably 1-20, more preferably 1-15, more preferably 1-10, more preferably 1-5 and even more preferably 1-3 amino acids to be substituted, deleted and/or added, relative to the sequence according to SEQ ID NO: 1. However, the catalytic activity must be at least maintained. Preference is given to an increase in the catalytic activity by suitable mutation or mutations.

The expression "aromatic" as used here encompasses substituted and unsubstituted aromatic hydrocarbon compounds, preferably unsubstituted hydrocarbon compounds. More preferably, the aromatic is a substituted or unsubstituted phenyl group. The expression "phenyl group" as used here encompasses substituted and unsubstituted phenyl groups, preferably an unsubstituted phenyl group. The expression "substituted" as used here preferably encompasses substitution by methoxy groups, halogens or hydroxyl groups, more preferably substitution by 1-3 methoxy groups, preferably by one methoxy group, by 1-3 halogens, preferably by one halogen, or by 1-3 hydroxyl groups, preferably by one hydroxyl group. The expression "heterocycle" as used here preferably encompasses heterocycles having 1-3, more preferably 1-2 and most preferably one atom(s) from the following group: oxygen, sulfur, nitrogen, selenium. The heterocycle is more preferably a 5-membered or 6-membered ring.

In the inventive reaction, 2-oxoalkanoates/-carboxylic acids are used as donor substrates, and undergo an "umpolung" reaction as a result of an enzyme-catalyzed nonoxidative decarboxylation. The nucleophilic carbanion which forms here can then add onto the β-carbon of the ketone in a 1,4 addition in the manner of a Stetter reaction.

The 2-oxoalkanoates/-carboxylic acids suitable here comprise straight-chain or branched, preferably straight-chain, saturated 2-oxoalkanoates/-carboxylic acids; the 2-oxoalkanoates/-carboxylic acids more preferably possess 3-12, more preferably 3-8, more preferably 3-6, more preferably 3-5, more preferably 3 or 4 and most preferably 3 carbon atoms. This preferably corresponds to the formula $R^4C(O)COO^-/R^4C(O)COOH$ with an $R^4$ radical having 1-10 carbon atoms, more preferably 1-6 carbon atoms, more preferably 1-4 carbon atoms, even more preferably 1-3 carbon atoms, more preferably 1 or 2 carbon atoms and most preferably 1 carbon atom.

The acceptor substrates or ketones suitable for the reaction include aliphatic, aromatic and heterocyclic α,β-unsaturated ketones. These ketones are illustrated by formula I.

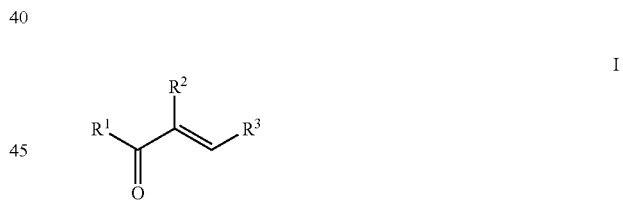

I

In Formula I, the Following Radicals are Preferred:
$R^1$ may be a straight-chain or branched, preferably straight-chain, $C_1$-$C_{10}$-alkyl radical or aromatic, where the aromatic is more preferably a phenyl group which may also be substituted;
$R^2$ may be a hydrogen, a $C_1$-$C_{10}$-alkyl radical or aromatic, more preferably a hydrogen or an aromatic, where the aromatic is more preferably a phenyl group;
$R^3$ may be a straight-chain or branched $C_1$-$C_{10}$-alkyl radical, a heterocycle or an aromatic, where the $C_1$-$C_{10}$-alkyl radical may in turn have a heterocycle or an aromatic, and where the heterocycle or the aromatic may be substituted by methoxy groups, halogens or hydroxyl groups;
$R^4$ may be a straight-chain or branched $C_1$-$C_{10}$-alkyl radical.

In Formula I, the Following Radicals are Even More Preferred:
$R^1$ may be a methyl group or phenyl group;
$R^2$ may be a hydrogen or aromatic, where the aromatic is more preferably a phenyl group;

$R^3$ may be a $C_1$-$C_{10}$-alkyl group, a heterocycle or a phenyl group which may be substituted by methoxy groups, halogens or hydroxyl groups, and $R^4$ is a $C_1$-$C_{10}$-hydrocarbon. The $C_1$-$C_{10}$-alkyl group here is preferably a saturated alkyl group.

In Formula I, the Following Radicals are Even More Preferred:

$R^1$ is a methyl group or a phenyl group.

$R^2$ is a hydrogen atom or aromatic, where the aromatic is more preferably a phenyl group, $R^3$ is a $C_1$-$C_{10}$-alkyl group, a heterocycle or a phenyl group, where the heterocycle or the phenyl group may be substituted by 1-3 methoxy groups, preferably by one methoxy group, by 1-3 halogens, preferably by one halogen, or by 1-3 hydroxyl groups, preferably by one hydroxyl group. The heterocycle here preferably has 1-3, more preferably 1-2 and most preferably 1 atom(s) from the following group: oxygen, sulfur, nitrogen, selenium. The heterocycle is more preferably a 5-membered or 6-membered ring.

By the inventive reaction, it is possible to prepare, from 2-oxoalkanoates/-carboxylic acids and the compounds of the formula I, using the PigD protein, compounds of the formula II.

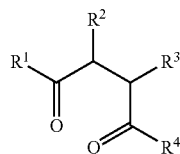

II

In Formula II, the Following Radicals are Preferred:

The $R^1$ to $R^3$ radicals correspond to the radicals as defined for formula I.

$R^4$ is preferably a straight-chain or branched, preferably straight-chain, hydrocarbon having 1-10 carbon atoms, more preferably 1-6 carbon atoms, more preferably 1-4 carbon atoms, even more preferably 1-3 carbon atoms, more preferably 1 or 2 carbon atoms and most preferably 1 carbon atom. $R^4$ is more preferably a saturated hydrocarbon.

The inventive 1,4 addition is additionally preferably performed with a quantitative ratio of donor substrate (2-oxoalkanoate/-carboxylic acid):acceptor substrate (ketone compound) of 3:1 to 1:3, more preferably 2:1 to 1:2, more preferably of 1.5:1 to 1:2 and most preferably of 1.5:1 to 1:1.

The 1,4 addition can be effected using solvents or solvent mixtures which are known to those skilled in the art. Preferably, a mixture of methyl tert-butyl ether or dimethyl sulfoxide and water is used (see example 1). The preparation of the PigD protein is described in the examples and is possible by techniques known to those skilled in the art. The procedure of the reactions is likewise described in the examples. The size of the reaction mixtures is not limited.

The 1,4 addition can preferably be performed with shaking or stirring at, for example, 30° C. In addition, it is preferred that initially only a portion of the PigD protein is added to the reaction mixture and, after a time of several hours, preferably after 10-25 hours, the remaining amount of PigD protein is added. The end of the reaction can be determined by customary methods, for example, GC-MS (gas chromatography coupled with mass spectrometry). The reaction mixture is preferably worked up after 10-45 hours, more preferably after 20-45 hours.

The reaction mixture can be worked up by known processes. This involves first removing the protein, for example by filtering it off with suction through a Celite pad, and transferring the crude product into the organic phase by washing with an organic solvent, for example, ethyl acetate. The organic phase can subsequently be dried, for example, over sodium sulfate and the solvent can be evaporated off under reduced pressure. The crude product can be purified by means of column chromatography (see example 1).

DESCRIPTION OF THE FIGURES

In FIG. 4, "scPDC" stands for Saccharomyces cerevisiae pyruvate decarboxylase. Reaction conditions: reaction volume 1.5 ml, 10% ethanol, 20 mM benzaldehyde derivative, 50 mM sodium pyruvate, 30 μl scPDC cell-free crude extrude (370 U/ml).

Figure 16:
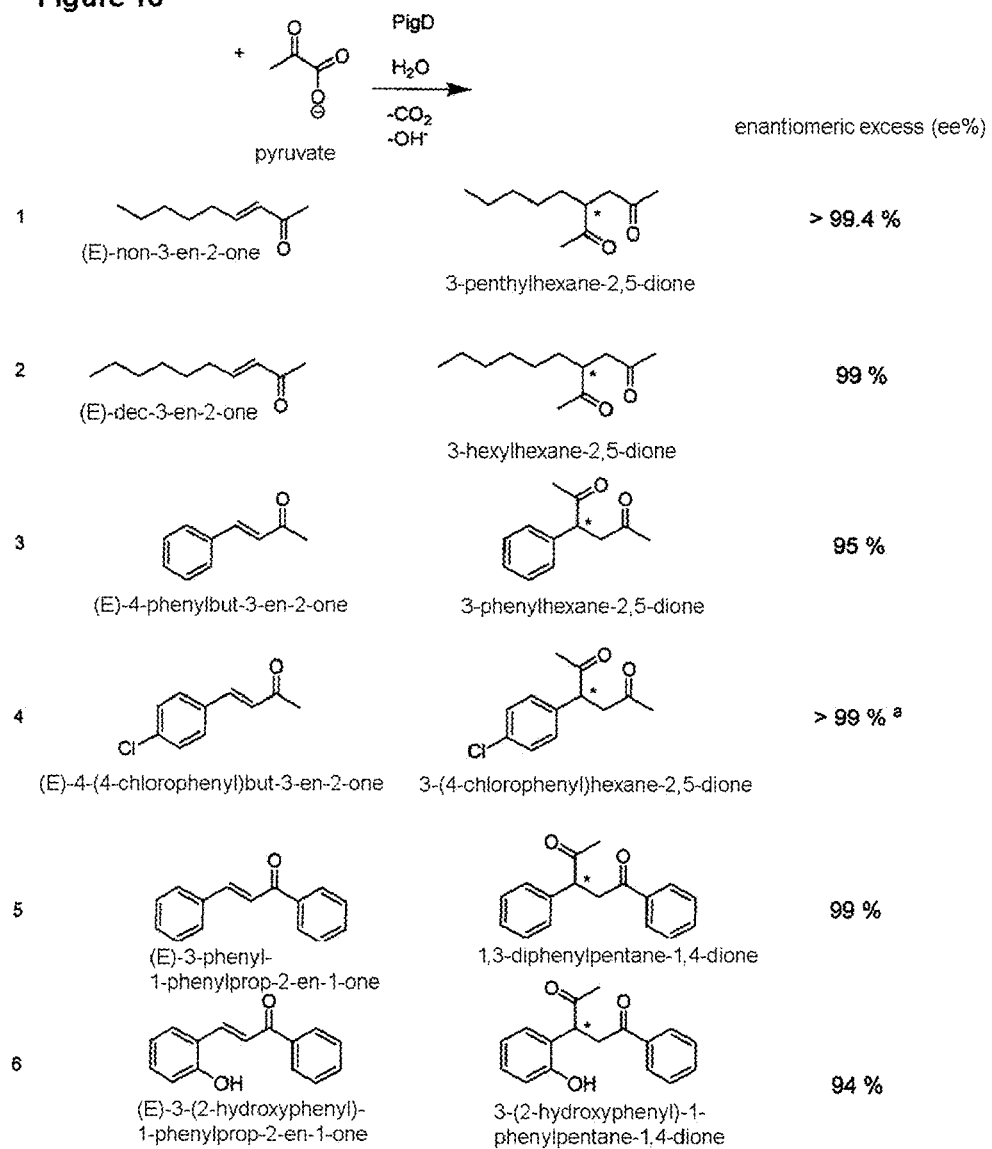
FIG. 16 shows the enantiomeric excesses of the products formed by the PigD catalysis.

Remark "a" in FIG. 16: Since only one peak was determined by various analysis methods, it was concluded that the enantiomeric excess of the enzymatically formed product here is ee>99%.

Figure 17:
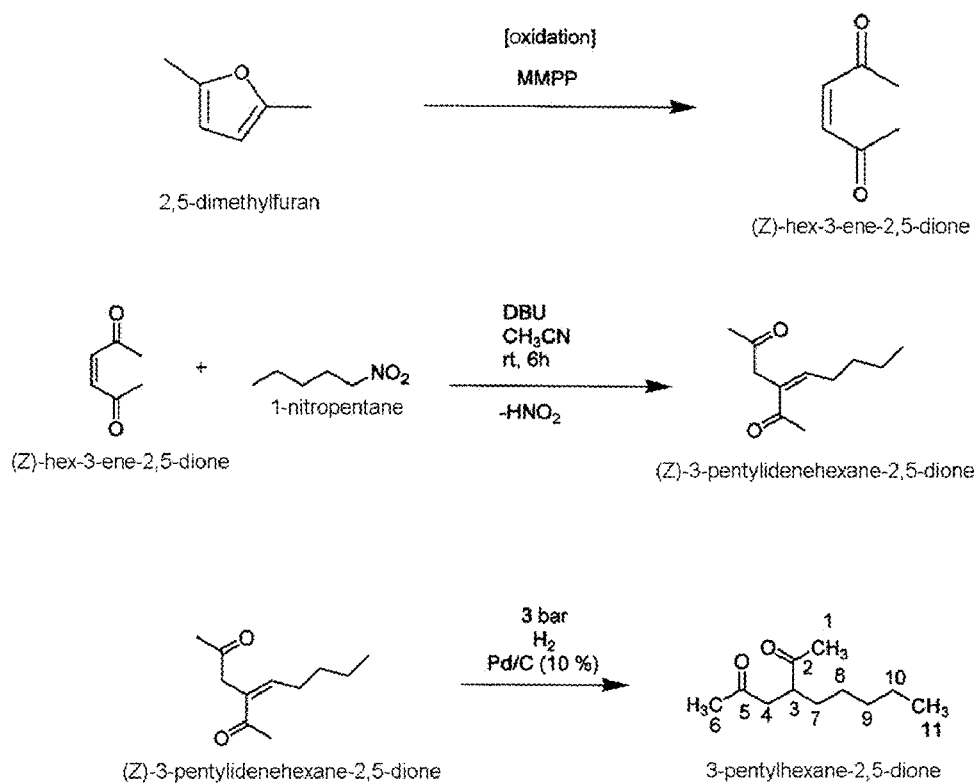

FIG. 17 shows the chemical synthesis of the racemic 3-pentylhexane-2,5-dione. The abbreviation MMPP stands for magnesium monoperoxyphthalate, DBU for 1,8-diazabicyclo[5.4.0] undec-7-ene.

Figure 18:
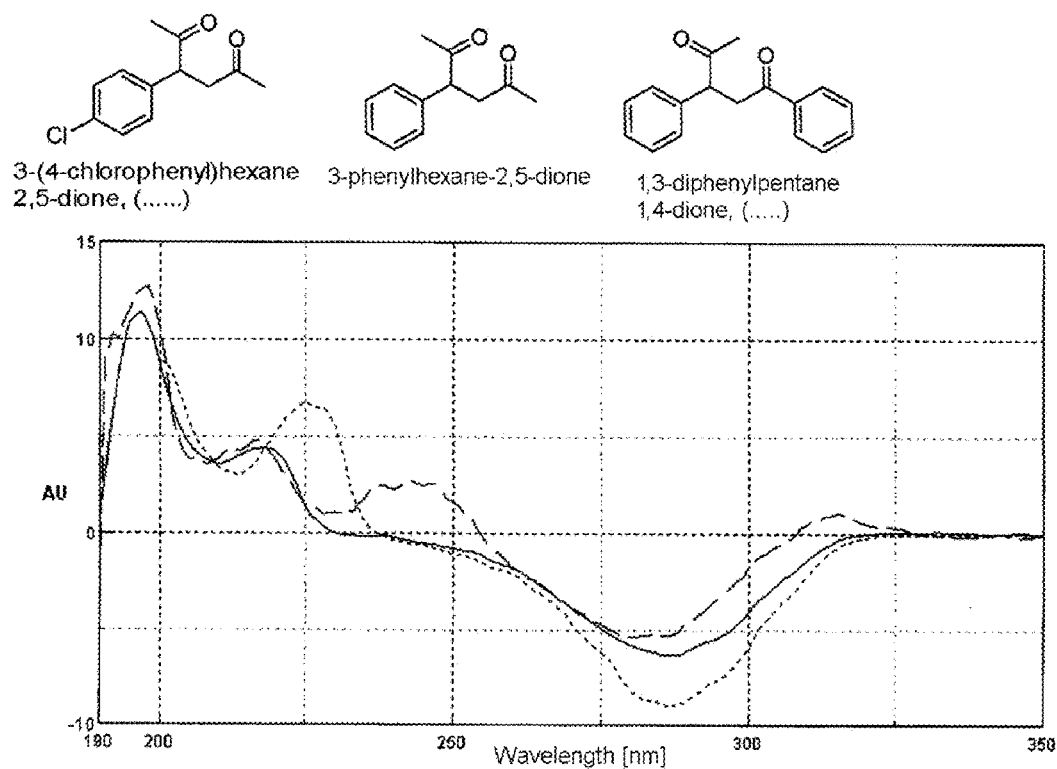

FIG. 18 shows the CD spectra of three products, which were prepared by PigD catalysis.

Figure 19:
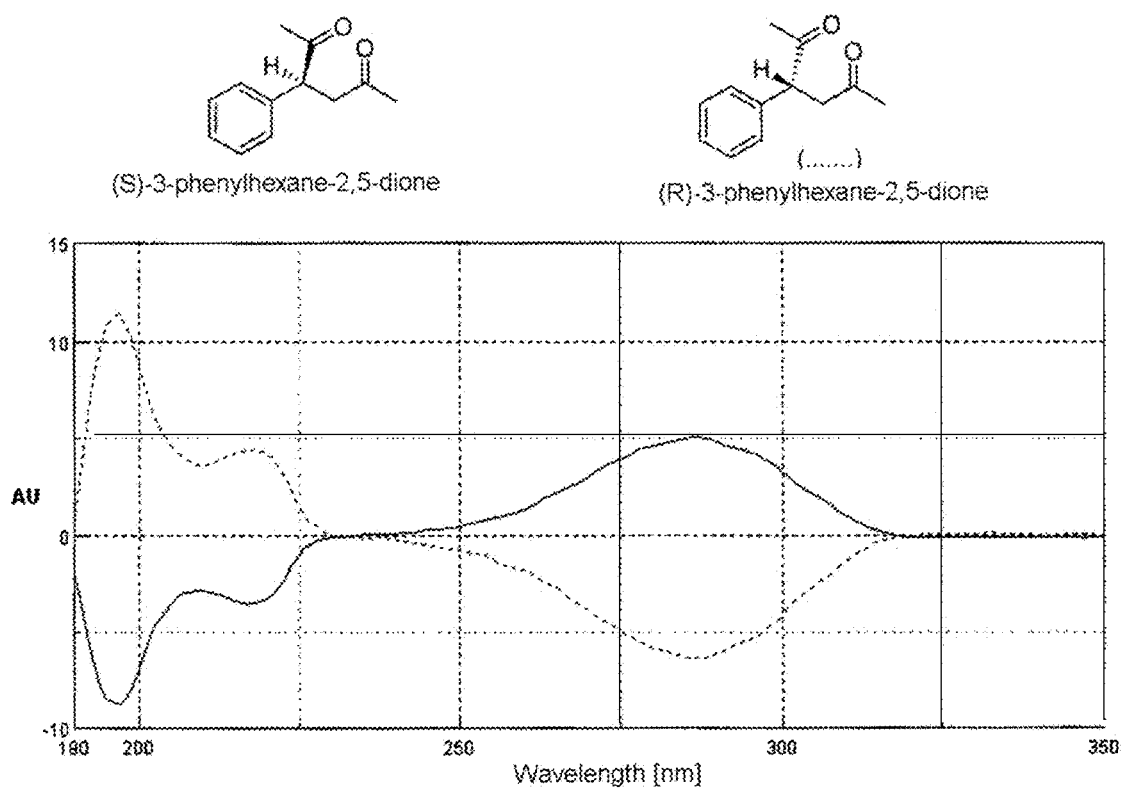

FIG. 19 shows the CD spectrum of (S)-3-phenylhexane-2,5-dione (prepared by chemical synthesis) and of (R)-3-phenylhexane-2,5-dione (prepared by PigD catalysis).

Figure 20:
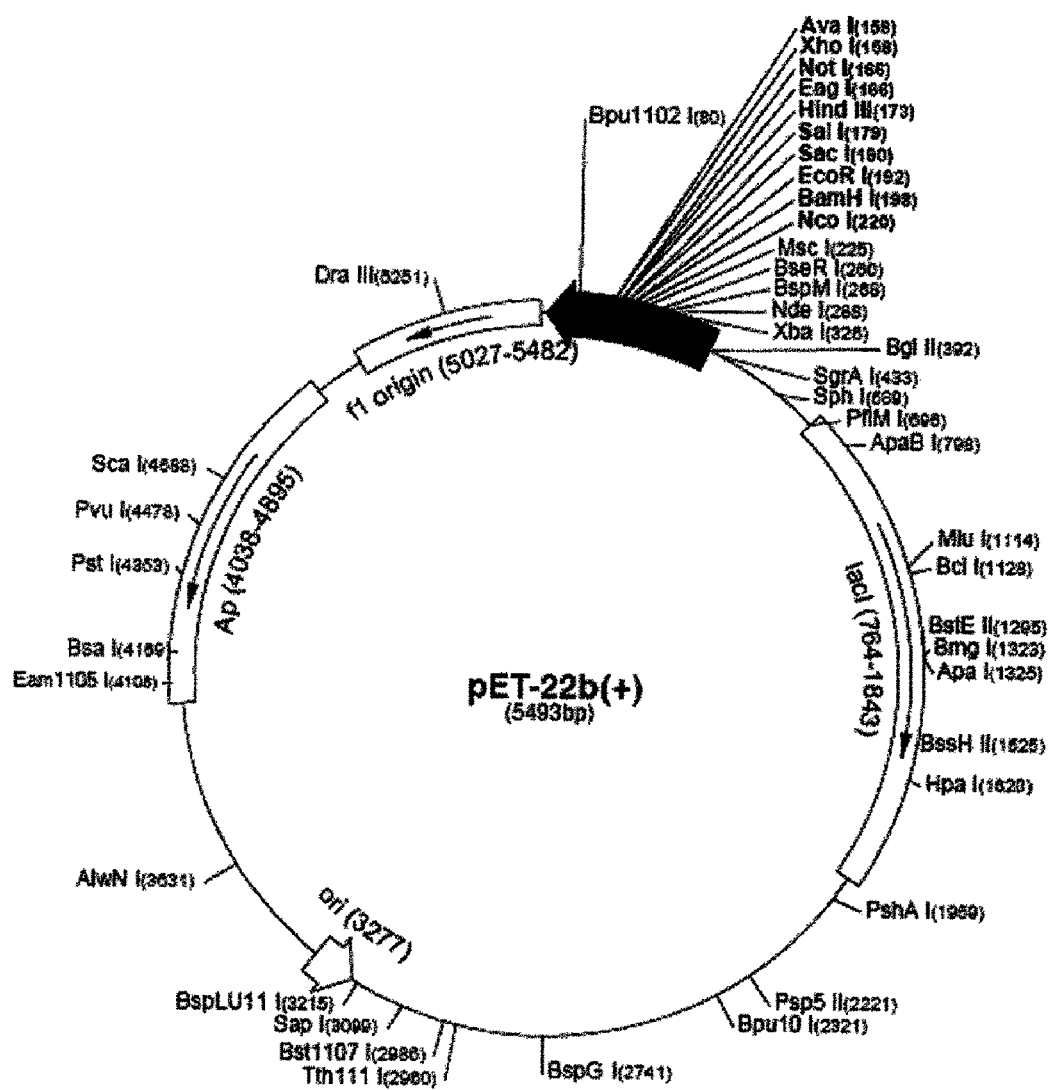

FIG. 20 shows the pET22b(+) vector (Novagen).

Figure 21:
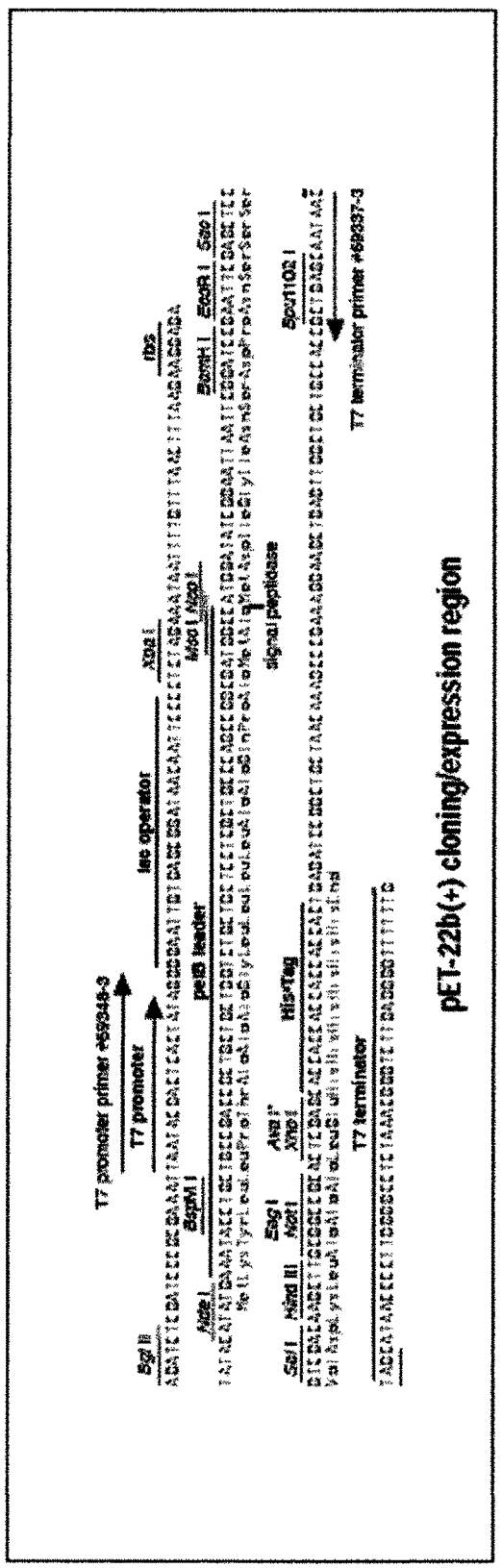

FIG. 21 shows the cloning sites of the pET22b(+) vector (Novagen).

Figure 22:
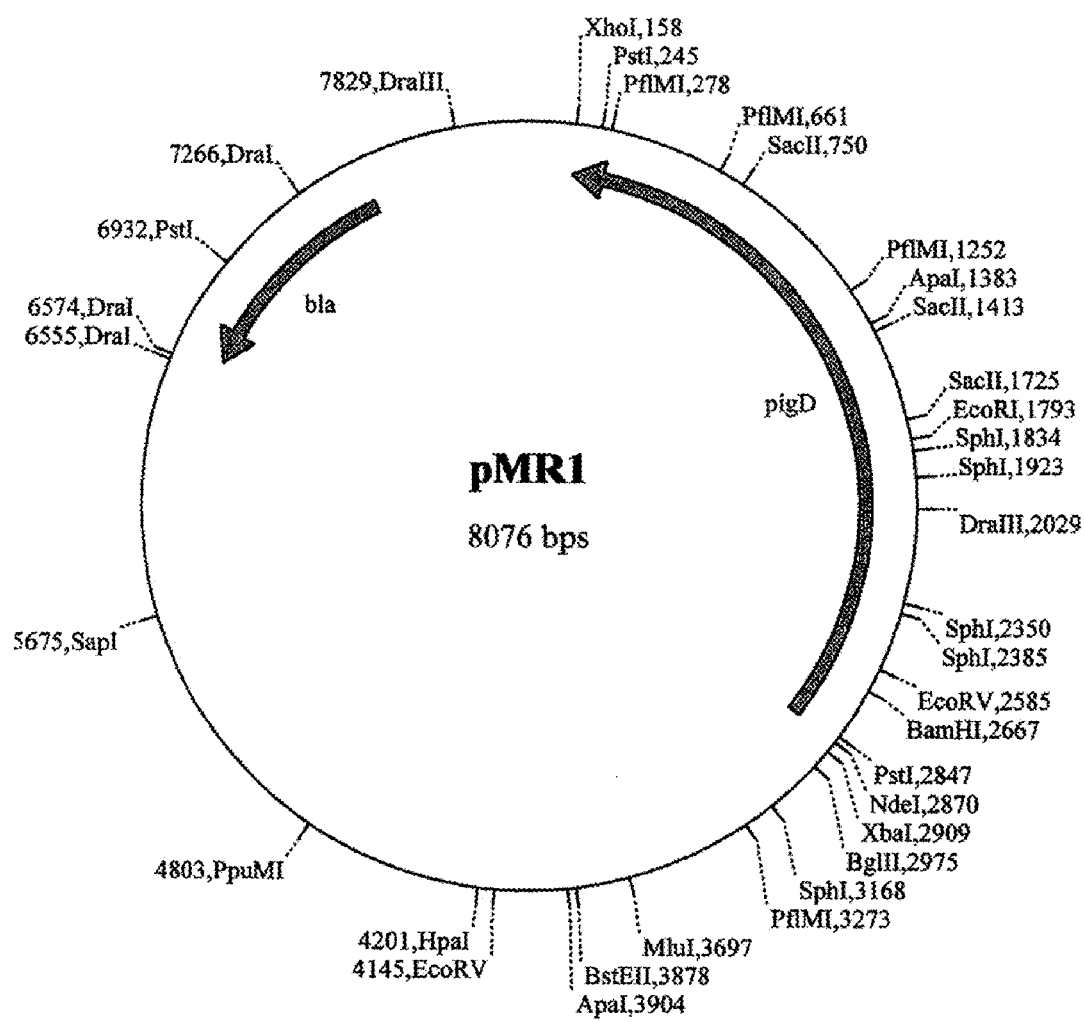

FIG. 22 shows the cloning vector (Novagen) into which the PigD obtained from *Serratia marcescens* has been inserted.

EXAMPLE 1

Reaction Conditions and Workup

The reactions were effected on the 12 ml scale but can be performed in any batch sizes.

In each case, 20 mM acceptor substrate and 25 mM sodium pyruvate were used. The substrates were dissolved in 600 µl of methyl tert-butyl ether, and 11.4 ml of demineralized water were added. After adding the lyophilized protein PigD, the mixture was shaken at 30° C. and 300 rpm.

In the mixtures for FIGS. 10, 12 and 13, 50% of the protein specified were added at the start, and the further 50% after 20 hours. The reaction mixture was worked up after 40 hours.

Figure 14:
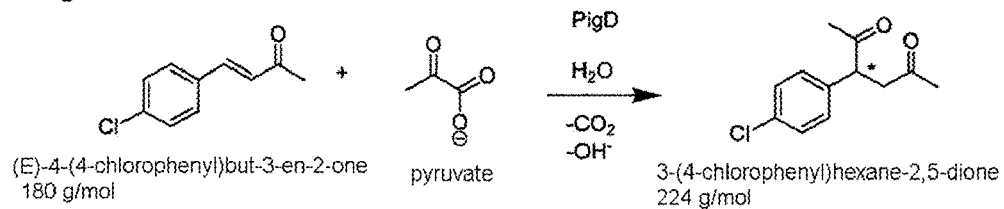
FIG. 14 shows the PigD-catalyzed conversion of (E)-4-(4-chlorophenyl)but-3-en-2-one to 3-(4-chlorophenyl) hexane-2,5-dione.
Figure 15:
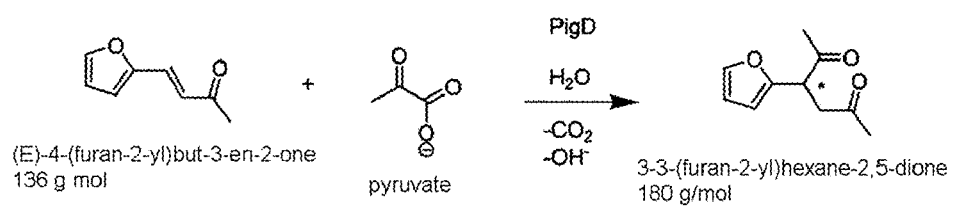
FIG. 15 shows the PigD-catalyzed conversion of (E)-4-(furan-2-yl)but-3-en-2-one to 3-(furan-2-yl)hexane-2,5-dione.

In the mixtures of FIGS. 14 and 15, all of the protein was added at time zero and workup was effected after 20 hours.

The protein lyophilizates contained 10% PigD protein. Reported at the bottom are the protein end concentrations actually present in the mixture.

Figure 10:
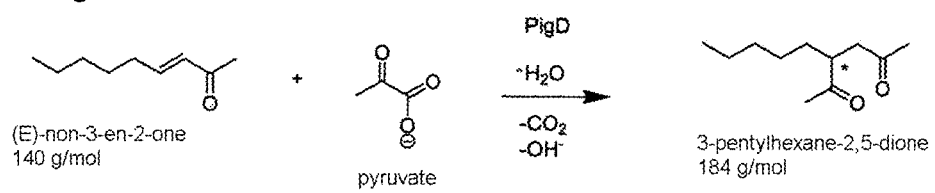
FIG. 10 shows the PigD catalyzed conversion of (E)-non-3-en-2-one to 3-pentylhexane-2,5-dione.

The desalinification in the course of protein purification was performed with the following buffer: 10 mM $KP_i$, 2.5 mM $MgSO_4$, 0.1 mM ThDP, 0.005 mM FAD, pH 7.0. It is thus possible to calculate the buffer concentration of the mixtures as follows:

FIG. 10:
Hours 1-20: 30 mM $KP_i$, 7.5 mM $MgSO_4$, 0.3 mM ThDP, 0.015 mM FAD
Hours 20-40: 60 mM $KP_i$, 15 mM $MgSO_4$, 0.6 mM ThDP, 0.03 mM FAD FIG. 12:
Hours 1-20: 43 mM $KP_i$, 11 mM $MgSO_4$, 0.4 mM ThDP, 0.02 mM FAD
Hours 20-40: 46 mM $KP_i$, 22 mM $MgSO_4$, 0.8 mM ThDP, 0.04 mM FAD FIG. 13:
Hours 1-20: 70 mM $KP_i$, 17.5 mM $MgSO_4$, 0.7 mM ThDP, 0.035 mM FAD
Hours 20-40: 140 mM $KP_i$, 35 mM $MgSO_4$, 1.4 mM ThDP, 0.07 mM FAD FIG. 14:
46 mM $KP_i$, 11.5 mM $MgSO_4$, 0.5 mM ThDP, 0.023 mM FAD FIG. 15:
83 mM $KP_i$, 20.75 mM $MgSO_4$, 0.83 mM ThDP, 0.04 mM FAD Workup:
The protein was removed by filtration with suction through a Celite pad, and the crude product was converted to the organic phase by washing with 60 ml of ethyl acetate. The organic phase was dried over $Na_2SO_4$, and the solvent was concentrated under reduced pressure. The crude product was purified by column chromatography ($SiO_2$, cyclohexane/ethyl acetate=5:1).

EXAMPLE 2

PigD Catalyzed Conversion of (E)-non-3-en-2-one to 3-pentylhexane-2,5-dione

Figure 11:
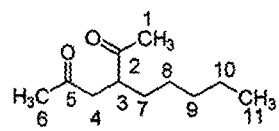
FIG. 11 shows the numbering scheme of 3-pentylhexane-2,5-dione.

The PigD-catalyzed conversion of (E)-non-3-en-2-one to 3-pentylhexane-2,5-dione is shown in FIG. 10. Reaction mixture and analysis of the product (see FIG. 11): 14 mg of protein; 48% yield of 3-pentylhexane-2,5-dione according to NMR analysis of the crude product; after purification by means of column chromatography ($R_f$(cyclohexane/ethyl acetate=5:1)=0.34): 17 mg of 3-pentylhexane-2,5-dione (38% yield);

GC-MS $R_t$=8.49 min. MS (70 eV, EI); m/z: 184 ([$M^+$], 1%), 169 ([$M^+$-$CH_3$], 3%), 141 ([$M^+$-$C_2H_3O$], 10%), 127 ([$M^+$-$C_3H_5O$], 25%), 114 ([$C_6H_{10}O_2^+$], 80%), 71 ([$C_5H_{11}^+$], 100%).

$^1$H NMR (400 MHz, $CDCl_3$): δ=3.07-2.98 (m, 1H, 3), 2.97 (dd, J=17.3 Hz, J=9.9 Hz, 1H, 4), 2.44 (dd, J=17.3 Hz, J=3.0 Hz, 1H, 4), 2.24 (s, 3H, 1), 2.15 (s, 3H, 6), 1.52-1.67 (m, 2H, 7), 1.20-1.35 (m, 6H, 8, 9, 10), 0.89 (t, 3H, 11).

$^{13}$C NMR (77.2 MHz, $CDCl_3$): δ=211.6, 207.5, 46.8 (4), 44.7 (3), 31.7 (8), 31.2 (7), 29.9 (6), 29.7 (1), 26.7 (9), 22.4 (10), 13.9 (11).

Chiral GC (FS-Lipodex D, isocratic, 90° C.) $R_t$=98.9 min (main enantiomer), 102.6 min (ent). ee=99.4% (according to column chromatography); ee>99.4% (extracted directly after 40 hours at 30° C.). The enantiomeric excess was determined by means of gas chromatography on a chiral phase with the chemically synthesized racemate as a reference.

EXAMPLE 3

PigD-Catalyzed Conversion of (E)-dec-3-en-2-one to 3-hexylhexane-2,5-dione

Figure 12:
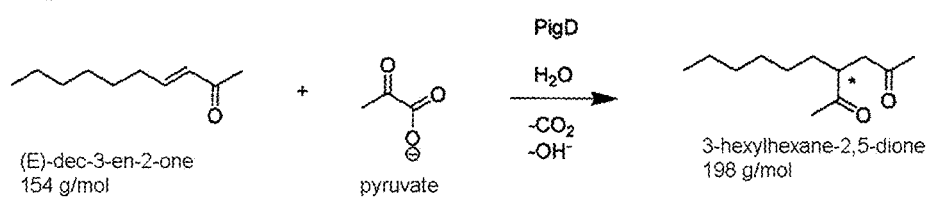
FIG. 12 shows the PigD-catalyzed conversion of (E)-dec-3-en-2-one to 3-hexylhexane-2,5-dione.

The PigD-catalyzed conversion of (E)-dec-3-en-2-one to 3-hexylhexane-2,5-dione is shown in FIG. 12. Reaction mixture and analysis of the product: 20.4 mg of protein; 30% 3-hexylhexane-2,5-dione in the crude product (GC-MS); after purification by means of column chromatography ($R_f$ (cyclohexane/ethyl acetate=5:1)=0.34): 14.5 mg of 3-hexylhexane-2,5-dione (30% yield).

GC-MS $R_t$=8.49 min. MS (70 eV, EI); m/z: 198 ([$M^+$], 1%), 183 ([$M^+$-$CH_3$], 1%), 155 ([$M^+$-$C_2H_3O$], 8%), 141 ([$M^+$-$C_3H_5O$], 21%), 127 ([$M^+$-$C_4H_6O$], 81%), 114 ([$C_6H_{10}O_2^+$], 81%), 71 ([$C_5H_{11}^+$], 100%).

Analysis of: $^1$H, (H,H)COSY, hsqc, hmbc, $^{13}$C dept NMR $^1$H NMR (400 MHz, $CDCl_3$): δ=3.08-2.98 (m, 1H, $CH_3COCH$), 2.97 (dd, J=17.2 Hz, 9.9 Hz, 1H, $CH_3COCH_2$), 2.44 (dd, J=17.2 Hz, 2.9 Hz, 1H, $CH_3COC\underline{H}_2$), 2.25 (s, 3H, COCH$_3$), 2.16 (s, 3H, COCH$_3$), 1.63-1.52 (m, 2H, CH$_3$COCHCH$_2$), 1.35-1.21 (m, 8H, CH$_3$(CH$_2$)$_4$), 0.89 (t, J=7.0 Hz, CH$_2$CH$_3$).

$^{13}$C NMR (100.6 MHz, CDCl$_3$): δ=211.5 (CO), 207.4 (CO), 46.8 (CH$_3$COCH), 44.7 (CH$_3$COCH$_2$), 31.5, 31.2 (CH$_3$COCHCH$_2$), 29.9 (COCH$_3$), 29.7 (COCH$_3$), 29.2, 27.0, 22.5, 14.0 (CH$_2$CH$_3$).

Chiral GC (FS-Lipodex D, isocratic, 90° C., only 1 peak after 187.1 min, 95° C., only 1 peak after 139.9 min, ee>99%).

$[α]_D^{20}$=−54 (α=−0.215, c=4 mg/ml, chloroform).

EXAMPLE 4

Figure 13:
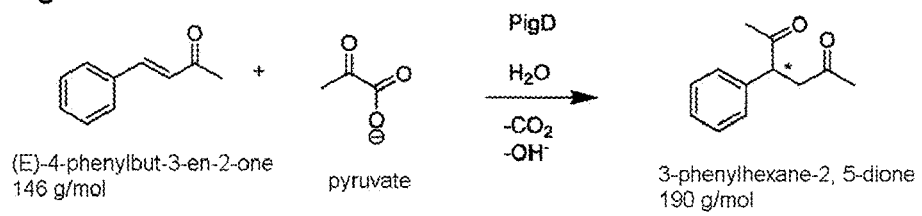
FIG. 13 shows the PigD-catalyzed conversion of (E)-4-phenylbut-3-en-2-one to 3-phenylhexane-2,5-dione.

PigD-Catalyzed Conversion of (E)-4-phenylbut-3-en-2-one to 3-phenylhexane-2,5-dione The PigD-catalyzed conversion of (E)-4-phenylbut-3-en-2-one to 3-phenylhexane-2,5-dione is shown in FIG. 13. Reaction mixture and analysis of the product: 33.7 mg of protein; 9% 3-phenylhexane-2,5-dione in the crude product (GC-MS); after purification by means of column chromatography (R$_f$(cyclohexane/ethyl acetate=5:1)=0.28): 3.4 mg of 3-phenylhexane-2,5-dione (7.4% yield).

GC-MS R$_t$=9.26 min. MS (70 eV, EI); m/z: 190 ([M$^+$], 75%), 172 ([M$^+$-H$_2$O], 19%), 148 ([M$^+$-C$_2$H$_2$O], 100%), 133 ([M$^+$-C$_3$H$_5$O], 28%), 115 (9%), 105 (C$_7$H$_5$O$^+$), 69%), 91 (19%), 77 ([C$_6$H$_5^+$], 31%).

Analysis of: $^1$H, (H,H)COSY, hsqc, hmbc, $^{13}$C NMR $^1$H NMR (400 MHz, CDCl$_3$): δ=7.38-7.27 (m, 3H, Ar), 7.24-7.19 (m, 2H, Ar), 4.24 (dd, J=10.2 Hz, 3.8 Hz, 1H, ArCH), 3.46 (dd, J=18.0 Hz, 10.2 Hz, 1H, CH$_2$), 2.59 (dd, J=18.0 Hz, 3.8 Hz, 1H, CH$_2$), 2.19 (s, 3H, COCH$_3$), 2.14 (s, 3H, COCH$_3$).

$^{13}$C NMR (100.6 MHz, CDCl$_3$): δ=207.1 (CO), 206.8 (CO), 137.8 (Ar, q), 129.1 (Ar, 2C), 128.2 (Ar, 2C), 127.5 (Ar), 53.9 (CH), 46.4 (CH$_2$), 29.9 (CH$_3$), 28.9 (CH$_3$).

CD(CH$_3$CN):
λ(nm) (Δε)=190 (0.9), 197 (11.5), 210 (3.6), 217 (4.4), 234 (−0.1), 287 (−6.3).

$[α]_D^{20}$=−300 (α=−0.300, c=1.0 mg/ml, chloroform).

Chiral HPLC-DAD
(HPLC method: Chiracel OD-H, 15° C., 0.70 ml·min$^{-1}$, n-hexane/2-propanol=97:3); R$_t$=29.3 min (ent) and 44.2 min (main enantiomer). ee=91% (after column chromatography).

Chiral LC-MS
(HPLC method: Chiracel OD-H, 20° C., 0.70 ml·min$^{-1}$, n-hexane/2-propanol=97:3); R$_t$=15.2 min (ent) and 21.3 min (main enantiomer), extracted mass+Q1: 191.0 amu; ee=95% (directly extracted after 16 hours at 30° C.).

EXAMPLE 5

PigD-Catalyzed Conversion of (E)-4-(4-chlorophenyl)but-3-en-2-one to 3-(4-chlorophenyl)-hexane-2,5-dione The PigD-catalyzed conversion of (E)-4-(4-chlorophenyl)but-3-en-2-one to 3-(4-chlorophenyl)-hexane-2,5-dione is shown in FIG. 14. Reaction mixture and analysis of the product: 11.3 mg of protein; 18% (E)-4-(4-chlorophenyl)but-3-en-2-one in the crude product (GC-MS); after purification by means of column chromatography (R$_f$(cyclohexane/ethyl acetate=5:1)=0.20): 7 mg of 3-(4-chloro-phenyl)hexane-2,5-dione (13% yield).

GC-MS R$_t$=10.44 min. MS (70 eV, EI); m/z: 226 (33%), 224 ([M$^+$], 100%), 208 (2%), 206 ([M$^+$-H$_2$O], 6%), 183 (25%), 182 (75%), 181 ([M$^+$-C$_2$H$_2$O], 50%), 169 (5%), 167 ([M$^+$-C$_3$H$_5$O], 15%), 147 (34%), 140 (10%), 138 ([M$^+$-C$_2$H$_2$O—C$_2$H$_3$O], 29%), 127 (8%), 125 [C$_7$H$_6$Cl$^+$], 25%), 115 (6%), 103 ([M$^+$-C$_2$H$_2$O—C$_2$H$_3$O—Cl], 40%), 77 (C$_6$H$_5^+$), 25%).

Analysis of: $^1$H, hsqc, $^{13}$C NMR $^1$H NMR (400 MHz, CDCl$_3$): δ=7.35-7.30 (m, 2H, Ar), 7.19-7.13 (m, 2H, Ar), 4.22 (dd, J=10.0 Hz, 4.1 Hz, 1H, ArCH), 3.42 (dd, J=18.0 Hz, 10.0 Hz, 1H, CH$_2$), 2.57 (dd, J=18.0 Hz, 4.1 Hz, 1H, CH$_2$), 2.18 (s, 3H, COCH$_3$), 2.14 (s, 3H, COCH$_3$).

$^{13}$C NMR (100.6 MHz, CDCl$_3$): δ=206.6 (CO), 206.3 (CO), 136.2 (Ar, q), 133.6 (Ar, q), 129.5 (Ar, 2C), 129.3 (Ar, 2C), 53.1 (CH), 46.3 (CH$_2$), 29.9 (CH$_3$), 28.9 (CH$_3$).

CD(CH$_3$CN): λ(nm) (Δε)=213 (3.1), 225 (6.7), 246 (−0.7), 287 (−8.9).

$[α]_D^{20}$=−314 (α=−1.571, c=5 mg/ml, chloroform).

Chiral HPLC
(HPLC method: Chiracel OD-H, 15° C., 0.50 ml·min$^{-1}$, n-hexane/2-propanol=99:1) R$_t$=45.3 min, only 1 peak (ee>98%).

EXAMPLE 6

PigD-Catalyzed Conversion of (E)-4-(furan-2-yl)but-3-en-2-one to 3-(furan-2-yl)hexane-2,5-dione The PigD-catalyzed conversion of (E)-4-(furan-2-yl)but-3-en-2-one to 3-(furan-2-yl)hexane-2,5-dione is shown in FIG. 15. Reaction mixture and analysis of the product: 20 mg of protein; 12% 3-(furan-2-yl)hexane-2,5-dione in the crude product (GC-MS); after purification by means of column chromatography (R$_f$(cyclohexane/ethyl acetate=5:1)=0.28): 3.3 mg of 3-(furan-2-yl)hexane-2,5-dione (6% yield).

GC-MS R$_t$=8.03 min. MS (70 eV, EI); m/z: 180 ([M$^+$], 100%), 162 ([M$^+$-H$_2$O], 5%), 137 ([M$^+$-C$_2$H$_3$O], 88%), 121 (5%), 109 (9%), 95 (63%), 81 (21%), 65 (29%).

Analysis of: $^1$H, hsqc, $^{13}$C NMR $^1$H NMR (400 MHz, CDCl$_3$): δ=7.34 (dd, J=1.9 Hz, 0.8 Hz, 1H, furanyl), 6.35 (dd, 3.2 Hz, 1.9 Hz, 1H, furanyl), 6.17 (d, J=3.2 Hz, 1H, furanyl), 4.36 (dd, J=9.8 Hz, 4.2 Hz, 1H, CH), 3.42 (dd, J=18.0 Hz, 9.8 Hz, 1H, CH$_2$), 2.68 (dd, J=18.0 Hz, 4.2 Hz, 1H, CH$_2$), 2.210 (s, 3H, COCH$_3$), 2.213 (s, 3H, COCH$_3$).

$^{13}$C NMR (100.6 MHz, CDCl$_3$): δ=206.1 (CO), 204.5 (CO), 171.1 (furanyl), 142.3 (furanyl), 110.6 (furanyl), 107.3 (furanyl), 47.2 (CH), 43.3 (CH$_2$), 29.8 (CH$_3$), 28.7 (CH$_3$).

EXAMPLE 7

Determination of the Enantiomeric Excess

The enantiomeric excess of the products formed by the PigD catalysis was determined by means of chiral GC-FID (gas chromatography separation with flame ionization detector), chiral HPLC-DAD (high-pressure liquid chromatography with diode array detector) or chiral LCMS (high-pressure liquid chromatography with mass spectrometry detection) with a photospray ion source (see FIG. 16).

EXAMPLE 8

Chemical Synthesis of the Reference Substance 3-pentylhexane-2,5-dione

In order to be able to analyze the addition product from example 2, racemic 3-pentylhexane-2,5-dione (see FIG. 17)

was prepared by chemical synthesis as a reference (Dominguez et al., Tetrahedron Letters 1990, 31, 7669; Ballini et al., Synthesis Stuttgart 2001, 2003).

Analysis data of 3-pentylhexane-2,5-dione:
GC-MS $R_t$=8.49 min. MS (70 eV, EI); m/z: 184 ([W], 1%), 169 ([M$^+$-CH$_3$], 3%), 141 ([M$^+$-C$_2$H$_3$O], 10%), 127 ([M$^+$-C$_3$H$_5$O], 25%), 114 ([C$_6$H$_{10}$O$_2$$^+$], 80%), 71 ([C$_5$H$_{11}$$^+$], 100%).

Analysis of: $^1$H, $^{13}$C, hsqc- and (H,H)-cosy NMR
$^1$H NMR (400 MHz, CDCl$_3$): δ=3.07-2.98 (m, 1H, 3), 2.97 (dd, J=17.3 Hz, J=9.9 Hz, 1H, 4), 2.44 (dd, J=17.3 Hz, J=3.0 Hz, 1H, 4), 2.24 (s, 3H, 1), 2.15 (s, 3H, 6), 1.52-1.67 (m, 2H, 7), 1.20-1.35 (m, 6H, 8, 9, 10), 0.89 (t, 3H, 11).
$^{13}$C NMR (77.2 MHz, CDCl$_3$): δ=211.6, 207.5, 46.8 (4), 44.7 (3), 31.7 (8), 31.2 (7), 29.9 (6), 29.7 (1), 26.7 (9), 22.4 (10), 13.9 (11).

Chiral GC (racemate); (FS-Lipodex D, isocratic, 90° C.) $R_t$=98.9 min, 102.6 min.

Equation 1 from FIG. 16:
Chiral Gas Chromatography
(FS-Lipodex D, isocratic, 90° C.),
$R_t$=98.9 min (main enantiomer), 102.6 min (ent).
ee=99.4% (after column chromatography)

The column chromatography and/or temperatures above 20° C. result in easy racemization owing to product instability. In this case, it is thus already possible to detect 0.3% of the opposite enantiomer by means of chiral GC. In the case of extraction of a sample with ethyl acetate without purification, after 40 hours of reaction time, no opposite enantiomer is detected by means of the chiral GC method developed.

The enantiomeric excess of the product formed enzymatically is thus: ee>99.4%.

The enantiomeric excess was determined by means of chiral gas chromatography with the chemically synthesized racemate as a reference.

Equation 2 from FIG. 16:
Chiral Gas Chromatography
(FS-Lipodex D, isocratic, 90° C.) only 1 peak after 187.1 min,
(FS-Lipodex D, isocratic, 95° C.) only 1 peak after 139.9 min,
Unless proven otherwise (see equation 1) the standard detection limit of chiral GC is 0.5%.

Since only one peak was detected by means of various GC analysis methods, it was concluded that the enantiomeric excess of the product formed enzymatically here is ee>99%.
Chiral LC-MS (MS (+Q1): 199 [M+1], 181 [M+1-H$_2$O]),
(HPLC method: Chiralpak AD, 20° C., 0.75 ml·min$^{-1}$, n-hexane/2-propanol=97:3)
$R_t$=10.4 min (main enantiomer), 20.4 min (ent),
enantiomeric excess of the product formed enzymatically: ee=99.1%.

Equation 3 from FIG. 16:
Chiral HPLC-DAD
(HPLC method: Chiracel OD-H, 15° C., 0.70 ml·min$^{-1}$, n-hexane/2-propanol=97:3),
$R_t$=29.3 min (ent) and 44.2 min (main enantiomer).
ee=91% (after column chromatography)
Chiral LC-MS (extracted mass+Q1: 191.0 amu),
(HPLC method: Chiracel OD-H, 20° C., 0.70 ml·min$^{-1}$, n-hexane/2-propanol=97:3)
$R_t$=15.2 min (ent) and 21.3 min (main enantiomer),
enantiomeric excess of the product formed enzymatically: ee=95% (extracted directly after 16 hours at 30° C.)

Equation 4 from FIG. 16:
Chiral HPLC-DAD
(HPLC method: Chiracel OD-H, 15° C., 0.50 ml·min$^{-1}$, n-hexane/2-propanol=99:1),
$R_t$=45.3 min, only 1 peak.
(The following HPLC analysis methods too always detect only 1 peak):
Chiracel OD-H, 15° C., 0.70 ml·min$^{-1}$, n-hexane/2-propanol=99:1, Chiracel OD-H, 15° C., 0.50 ml·min, n-hexane/2-propanol=97:3, Chiracel OD-H, 15° C., 0.50 ml·min$^{-1}$, n-hexane=100, Chiralpak AD, 20° C., 0.75 ml·min$^{-1}$, n-hexane/2-propanol=95:5, Chiralpak AD, 20° C., 0.75 ml·min$^{-1}$, n-hexane/2-propanol=97:3, Chiralpak AD, 20° C., 0.75 ml·min$^{-1}$, n-hexane/2-propanol=99:1, Chiralpak AD, 20° C., 0.75 ml·min$^{-1}$, n-hexane=100, Chiracel OB, 20° C., 0.75 ml·min$^{-1}$, n-hexane/2-propanol=90:10, Chiracel OB, 20° C., 0.75 ml·min$^{-1}$, n-hexane/2-propanol=95:5, Chiracel OB, 20° C., 0.75 ml·min$^{-1}$, n-hexane/2-propanol=97:3.
Chiral LC-MS (MS (+Q1): 225 [M+1], 207 [M+1-H$_2$O]),
(HPLC method: Chiralpak AD, 20° C., 0.75 ml·min$^{-1}$, n-hexane/2-propanol=95:5),
$R_t$=11.0 min, only 1 peak.
Unless proven otherwise, the standard detection limit of chiral LC-MS with a photospray ion source is 0.5%. Since only one peak was detected by means of various analysis methods, it was concluded that the enantiomeric excess of the product formed enzymatically here is ee>99%.

Equation 5 from FIG. 16:
Chiral LC-MS (MS (+Q1): 253 [M+1], 235 [M+1-H$_2$O]),
(HPLC method: Chiralpak AD, 20° C., 0.75 ml·min$^{-1}$, n-hexane/2-propanol=95:5), $R_t$=17.6 min (ent) 19.5 (main enantiomer),
enantiomeric excess of the product formed enzymatically: ee=99%.

Equation 6 from FIG. 16:
Chiral HPLC
(HPLC method: Chiracel OD-H, 25° C., 0.75 ml·min$^{-1}$, n-hexane/2-propanol=96:4), $R_t$=58.8 min (main enantiomer), 65.0 min (ent).
ee=81% (after column chromatography)
Enantiomeric excess of the product formed enzymatically: ee=94% (extracted directly after 16 hours at 30° C.).

EXAMPLE 9

Determination of the Absolute Configuration Using Chemically Synthesized (S)-3-phenylhexane-2,5-dione as a Comparison To determine the absolute configuration of the product from example 4, a chemical synthesis of (S)-3-phenylhexane-2,5-dione was carried out (Clark et al., Journal of Organic Chemistry 1970, 35, 1114).

(S)-3-Phenylhexane-2,5-dione was synthesized from (S)-2-phenylsuccinic acid with methyllithium in diethyl ether. The analytical data apart from the optical rotation and CD corresponds to the product formed by means of PigD catalysis (FIGS. 10 and 16).

$R_f$(SiO$_2$, cyclohexane:ethyl acetate=10:1)=0.23.
GC-MS $R_t$=9.26 min. MS (70 eV, EI); m/z: 190 ([M$^+$] 75%), 172 ([M$^+$-H$_2$O], 19%), 148 ([M$^+$-C$_2$H$_2$O], 100%), 133 ([M$^+$-C$_3$H$_5$O], 28%), 115 (9%), 105 ([C$_7$H$_5$O$^+$], 69%), 91 (19%), 77 ([C$_6$H$_5$$^+$], 31%).
$^1$H NMR (400 MHz, CDCl$_3$) δ=7.38-7.27 (m, 3H, Ar), 7.24-7.19 (m, 2H, Ar), 4.24 (dd, J=10.2 Hz, 3.8 Hz, 1H, ArCH), 3.46 (dd, J=18.0 Hz, 10.2 Hz, 1H, CH$_2$), 2.59 (dd, J=18.0 Hz, 3.8 Hz, 1H, CH$_2$), 2.19 (s, 3H, COCH$_3$), 2.14 (s, 3H, COCH$_3$).

$^{13}$C NMR (100.6 MHz, CDCl$_3$) δ=207.1 (CO), 206.8 (CO), 137.8 (Ar, q), 129.1 (Ar, 2C), 128.2 (Ar, 2C), 127.5 (Ar), 53.9 (CH), 46.4 (CH$_2$), 29.9 (CH$_3$), 28.9 (CH$_3$).

Chiral HPLC-DAD (HPLC method: Chiracel OD-H, 15° C., 0.70 ml·min$^{-1}$, n-hexane/2-propanol=97:3), R$_t$=29.3 min (main enantiomer), 44.2 min (ent).

ee=75% (after column chromatography)

Chiral LC-MS (extracted mass+Q1: 191.0 amu), (HPLC method: Chiracel OD-H, 20° C., 0.70 ml·min$^{-1}$, n-hexane/2-propanol=97:3)

R$_t$=15.2 min (main enantiomer) and 21.3 min (ent), ee=75% (after column chromatography).

CD (CH$_3$CN):

λ (nm) (Δε)=197 (−8.7), 209 (−2.9), 217 (−3.5), 239 (0.1), 286 (5.1).

$[α]_D^{20}$=+173 (α=+0.104, c=0.6 mg/ml, chloroform).

Optical Rotation and CD (Circular Dichroism)

Figure 1:
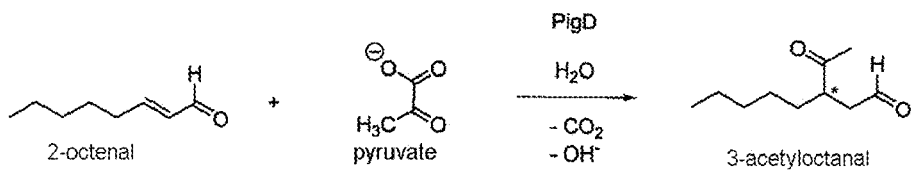
FIG. 1 shows the reaction, postulated by Salmond et al., of 2-octenal with pyruvate under PigD catalysis.
Figure 2:
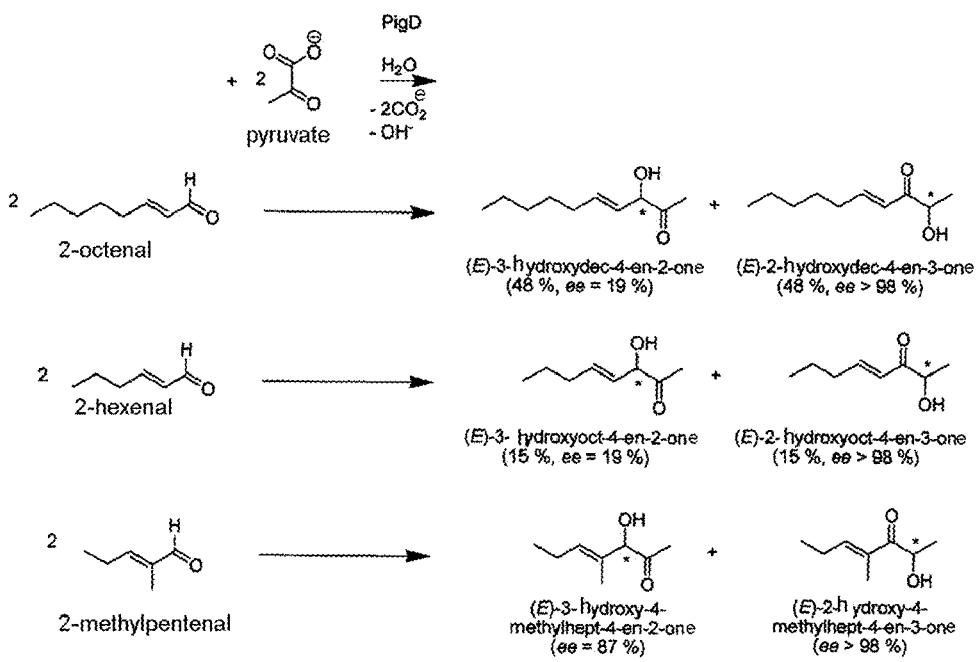
FIG. 2 shows the PigD-catalyzed reaction of 2-octenal, 2-hexenal and 2-methylpentenal with pyruvate. The product formation in percent (determined by means of NMR—nuclear magnetic resonance) and the enantiomeric excess (determined by means of chiral HPLC—high performance liquid chromatography) are reported in brackets.
Figure 3:
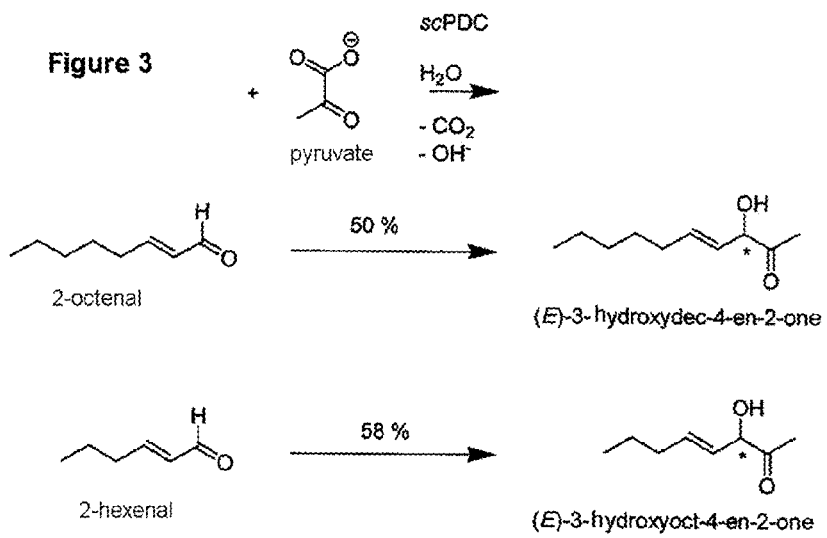
FIG. 3 shows the addition of pyruvate onto α,β-unsaturated aliphatic aldehydes with catalysis by a pyruvate decarboxylase, for example from Saccharomyces cerevisiae. The percentages of the yields for pyruvate decarboxylase from Saccharomyces cerevisiae are shown in the figure on the reaction arrows.
Figure 4:
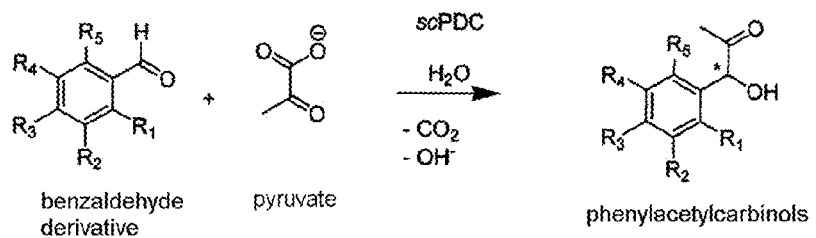
FIG. 4 shows scPDC-catalyzed reactions with benzaldehyde and benzaldehyde derivatives.
Figure 5:
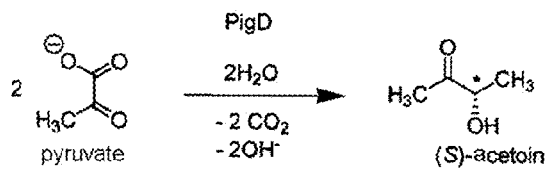
FIG. 5 shows the PigD-catalyzed conversion of pyruvate to acetoin (ee (S)-acetoin=70%, chiral GC (FS-Lipodex D, 70° C., $R_t$=13.7 min (R), 18.3 (S))).
Figure 6:
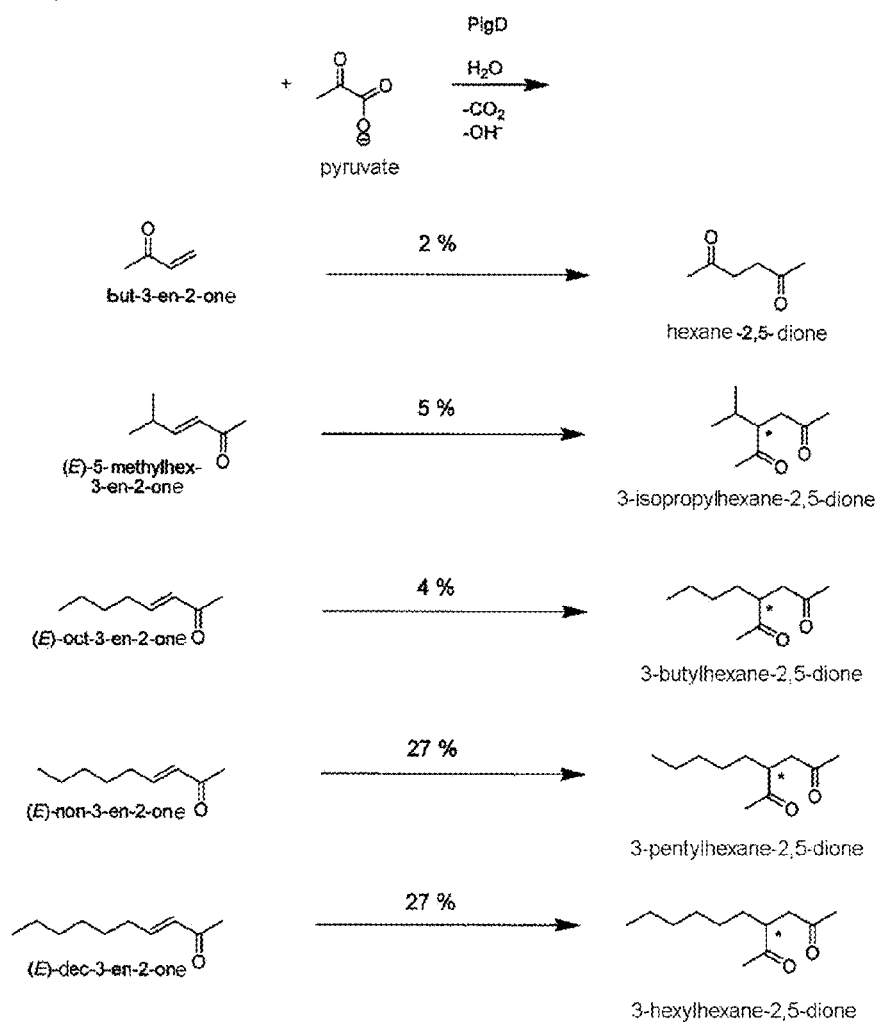
FIG. 6 shows the use of α,β-unsaturated aliphatic ketones as the acceptor substrate. Product formation is reported in percent (determined by means of NMR). In these reactions, the reaction mixture was composed of: reaction volume 1.5 ml, 20% DMSO (dimethyl sulfoxide), 20 mM acceptor substrate, 25 mM sodium pyruvate, 1100 μg of PigD protein.

Optical rotation of the product resulting from PigD catalysis:

3-hexylhexane-2,5-dione (FIG. 6):

$[α]_D^{20}$=−54 (α=−0.215, c=4 mg/ml, chloroform).

Figure 7:
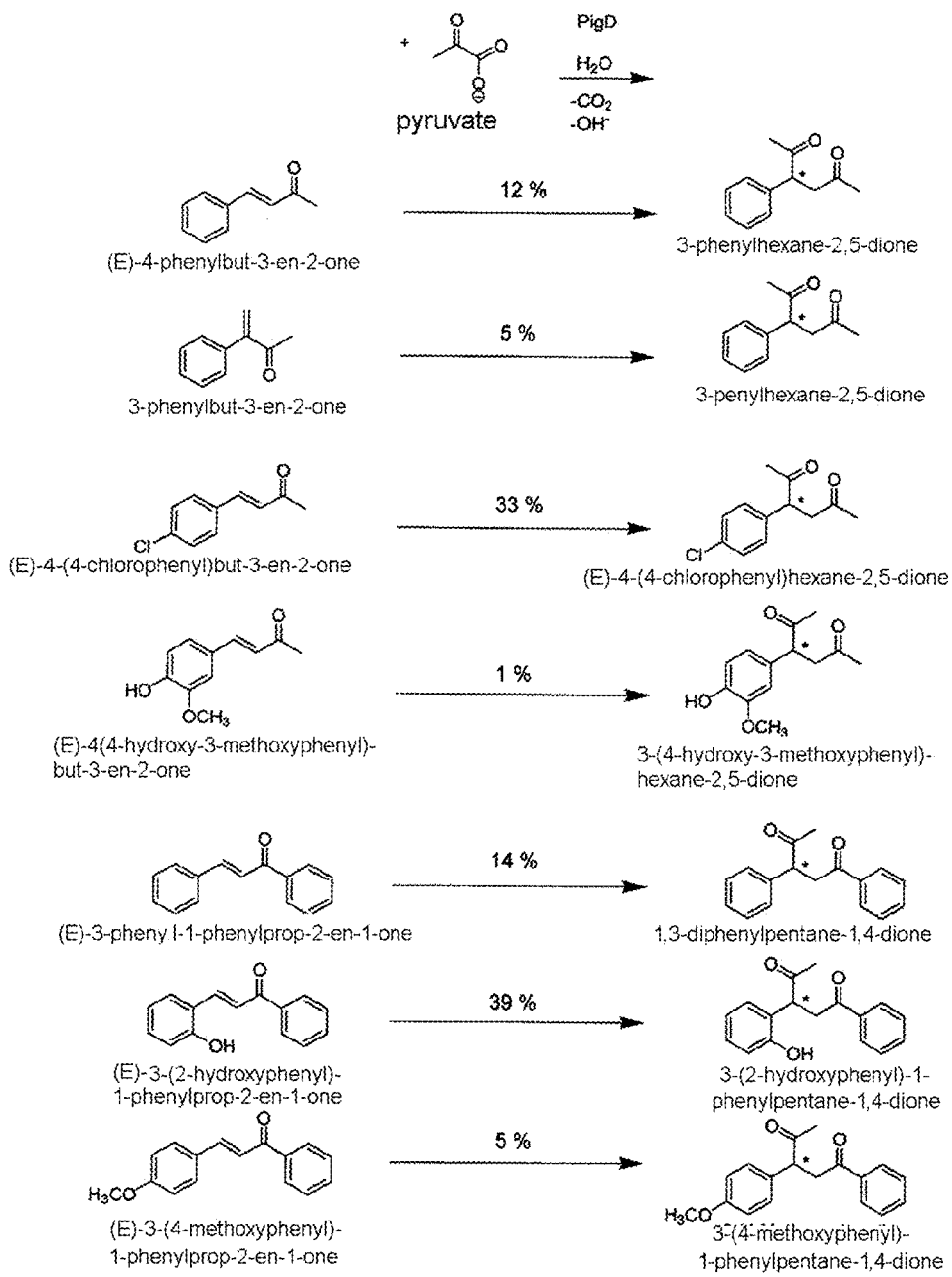
FIG. 7 shows the use of α,β-unsaturated aromatic ketones as the acceptor substrate. Product formation is reported in percent (determined by means of NMR). The reaction mixture in these reactions was composed of: reaction volume 1.5 ml, 20% DMSO, 20 mM acceptor substrate, 25 mM sodium pyruvate, 1100 μg of PigD protein.
Figure 8:
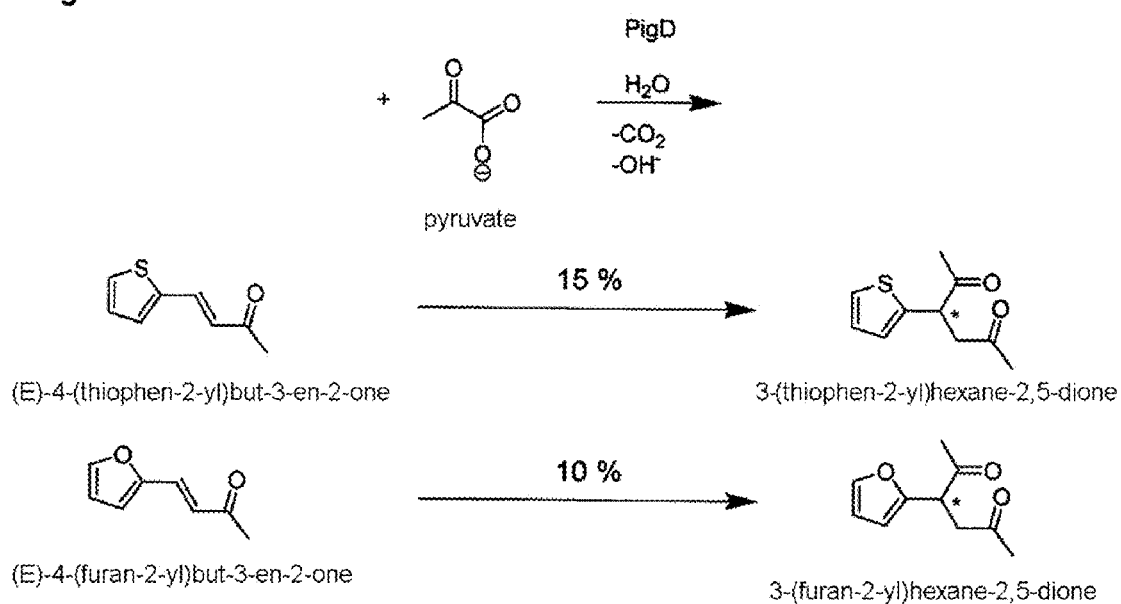
FIG. 8 shows the 1,4 addition of pyruvate on to α,β-unsaturated heterocyclic ketones. Product formation, determined by means of NMR, is reported here on the reaction arrow in percent. The reaction mixture in these reactions was composed of: reaction volume 1.5 ml, 20% DMSO, 20 mM acceptor substrate, 25 mM sodium pyruvate, 1100 μg of PigD protein.
Figure 9:
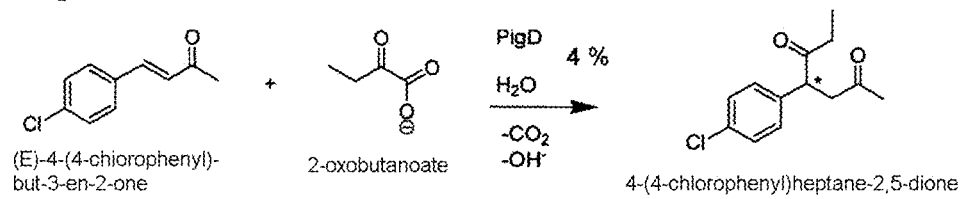
FIG. 9 shows the use of 2-oxobutanoate as the donor substrate. Product formation, determined by means of NMR, is reported here on the reaction arrow in percent. The reaction mixture in this reaction was: reaction volume 1.5 ml, 20% DMSO, 20 mM acceptor substrate, 25 mM 2-oxobutanoate, 1100 μg of PigD protein.

3-phenylhexane-2,5-dione (FIG. 7):

$[α]_D^{20}$=−300 (α=−0.300, c=1.0 mg/ml, chloroform).

3-(4-chlorophenyl)hexane-2,5-dione (FIG. 7):

$[α]_D^{20}$=−314 (α=−1.571, c=5 mg/ml, chloroform).

1,3-diphenylpentane-1,4-dione (FIG. 7):

$[α]_D^{25}$=−179 (α=−0.357, c=2 mg/ml, chloroform).

Optical rotation of (S)-3-phenylhexane-2,5-dione (FIG. 7):

$[α]_D^{20}$=+173 (α=+0.104, c=0.6 mg/ml, chloroform).

Absolute Configuration

Separation on chiral phase by means of HPLC-MS showed that, as a result of PigD catalysis, the opposite enantiomer to the chemically synthesized (S)-3-phenylhexane-2,5-dione is formed in a very large enantiomeric excess. The optical rotations and CD spectra of the chemically synthesized (S)-3-phenylhexane-2,5-dione were compared to those of the products which were obtained by PigD catalysis, and the results obtained for the chiroptic properties were the mirror image.

This information leads to the conclusion that the asymmetric intermolecular Stetter reaction catalyzed by the PigD enzyme affords products with R configuration when R$^3$ is an aromatic (R$^3$ bonded via an sp$^2$-hybridized carbon). In the case of an aliphatic (R$^3$ bonded via an sp$^a$-hybridized carbon), the determination of configuration is formally reversed.

EXAMPLE 10

Preparation of the PigD Protein

Cloning:

The starting material for the studies was the genomic DNA from *Serratia marcescens*. By means of PCR (polymerase chain reaction) the DNA which corresponds to the PigD protein from *Serratia marcescens* was amplified. The primers used also generated an NdeI restriction cleavage site at the 5' end, and an XhoI restriction cleavage site at the 3' end. The vector pET22b(+) (FIG. 20) possesses these two cleavage sites in its multi-cloning site (MCS) (FIG. 21). Both the vector and the particular PCR product were then digested with the two restriction enzymes and, thereafter, ligated with T4 DNA ligase.

The vector thus obtained (FIG. 22) was used to transform *E. coli* DH5α for vector production, and *E. coli* XL1blue, or *E. coli* BL21(DE3)plysS, *E. coli* BL21(DE3)*CP and *E. coli* BL21(DE3) cells for expression. In this way, a fusion protein of PigD from *Serratia marcescens* was obtained as a C-terminally His-Tagged protein. The amino acid sequence obtained is shown as amino acid sequence SEQ ID NO: 1 in the sequence listing.

Expression:

The best expression was obtained in *E. coli* BL21(DE3) cells. The cells were incubated in LB medium (100 μg/ml of ampicillin) at 37° C. and 120 rpm in shaking flasks and, after adding IPTG (0.4 mM), expressed at 29° C. overnight. In addition, a fermenter run was carried out, which had a lower expression.

Protein Purification:

The protein purification was carried out by means of immobilized metal ion affinity chromatography. Both Talon® beads and nickel-NTA Sepharose were used.

The invention claimed is:

1. A process for preparing a compound of the formula II

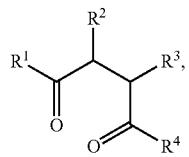

comprising the steps of:
reacting an α,β-unsaturated ketone compound of the formula I,

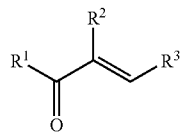

with donor substrates using a PigD protein as a catalyst to effect 1,4 additions of said substrates onto said compound of formula I, wherein said donor substrates comprise straight-chain, saturated 2-oxoalkanoates or 2-oxocarboxylic acids with 1-10 carbon atoms and comprising the formula $R^4C(O)COO^-$ or $R^4C(O)COOH$, respectively, in which $R^1$ is a straight-chain or branched $C_1$-$C_{10}$-alkyl radical or an aromatic comprising a substituted or unsubstituted phenyl group, $R^2$ is a hydrogen, $C_1$-$C_{10}$-alkyl radical or an aromatic comprising a substituted or unsubstituted phenyl group;

$R^3$ is a straight-chain or branched $C_1$-$C_{10}$-alkyl radical, a heterocycle comprising a substituted or unsubstituted phenyl group or an aromatic comprising a substituted or unsubstituted phenyl group, where the $C_1$-$C_{10}$-alkyl radical may in turn have a heterocycle comprising a 5- or 6-membered heterocyclic ring or an aromatic comprising a substituted or unsubstituted phenyl group, and where the heterocycle or the aromatic may be substituted by methoxy groups, halogens or hydroxyl groups, and $R^4$ is a straight-chain or branched $C_1$-$C_{10}$-alkyl radical.

2. The process as claimed in claim 1, characterized in that $R^1$ is a methyl group or an aromatic comprising a substituted or unsubstituted phenyl group, $R^2$ is a hydrogen or an aromatic comprising a substituted or unsubstituted phenyl group, and $R^3$ is a $C_1$-$C_{10}$-alkyl group, a heterocycle comprising a substituted or unsubstituted phenyl group or an aromatic comprising a substituted or unsubstituted phenyl group, where the heterocycle or the aromatic may be substituted by methoxy groups, halogens or hydroxyl groups, and in which $R^4$ may be a $C_1$-$C_{10}$-hydrocarbon.

3. The process as claimed in claim 1, characterized in that the 1,4 additions of donor substrates catalyzed by the PigD protein are effected enantioselectively with an enantiomeric excess of more than 80% ee.

4. The process as claimed in claim 1, characterized in that said 2-oxoalkanoates or 2-oxocarboxylic acid donor substrates of the formula $R^4C(O)COO^-$ or $R^4C(O)COOH$ are selected from the group consisting of pyruvate, pyruvic 2-oxobutanoate and 2-oxybutyric acid, wherein $R^4$ is methyl or ethyl.

5. A process for catalyzing 1,4 additions of 2-oxoalkanoates/2-carboxylic acids of the formula $R^4C(O)COO^-$ or $R^4C(O)COOH$, wherein $R^4$ is a straight-chain or branched $C_1$-$C_{10}$-alkyl radical, onto α,β-unsaturated ketones of the formula I

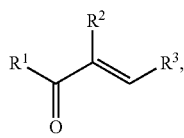

in which $R^1$ is a straight-chain or branched $C_1$-$C_{10}$-alkyl radical or an aromatic comprising a substituted or unsubstituted phenyl group, $R^2$ is a hydrogen, $C_1$-$C_{10}$-alkyl radical or an aromatic comprising a substituted or unsubstituted phenyl group, and $R^3$ is a straight-chain or branched $C_1$-$C_{10}$-alkyl radical, a heterocycle comprising a 5- or 6-membered heterocyclic ring or an aromatic comprising a substituted or unsubstituted phenyl group, where the $C_1$-$C_{10}$-alkyl radical may in turn have a heterocycle comprising a 5- or 6-membered heterocyclic ring or an aromatic comprising a substituted or unsubstituted phenyl group, and where the heterocycle or the aromatic may be substituted by methoxy groups, halogens or hydroxyl groups, said process comprising the steps of:

reacting the 2-oxoalkanoates/2-carboxylic acids selected from the group consisting of pyruvate, pyruvic acid, 2-oxobutanoate and 2-oxobutyric acid and α,β-unsaturated ketones of the formula I in the presence of a PigD protein catalyst to effect 1,4 additions with $CO_2$ elimination.

6. The process as claimed in claim 5, characterized in that the 1,4 additions are effected enantioselectively with an enantiomeric excess of the addition products of more than 80% ee.

7. The process as claimed in claim 5, characterized in that aliphatic, aromatic and heterocyclic α,β-unsaturated ketones of the formula I are used, in which $R^1$ is a methyl group or an aromatic comprising a substituted or unsubstituted phenyl group, $R^2$ is a hydrogen atom, $C_1$-$C_{10}$ alkyl radical or an aromatic comprising a substituted or unsubstituted phenyl group, and $R^3$ is a $C_1$-$C_{10}$-alkyl group, a heterocycle comprising a 5- or 6-membered heterocyclic ring or an aromatic comprising a substituted or unsubstituted phenyl group, where the heterocycle and the aromatic may be substituted by methoxy groups, halogens or hydroxyl groups.

* * * * *